United States Patent
Lim et al.

(10) Patent No.: US 10,130,653 B2
(45) Date of Patent: Nov. 20, 2018

(54) BIODEGRADABLE CONTROL OF BACTERIAL CELLULOSE BY RADIATION TECHNOLOGY AND ABSORBABLE PERIODONTAL MATERIAL USING SAME

(71) Applicant: KOREA ATOMIC ENERGY RESEARCH INSTITUTE, Daejeon (KR)

(72) Inventors: Youn-Mook Lim, Jeollabuk-do (KR); Sung In Jeong, Chungcheongbuk-do (KR); Hui-Jeong Gwon, Jeollabuk-do (KR); Jong Seok Park, Jeollabuk-do (KR); Jung-Bo Huh, Busan (KR)

(73) Assignee: KOREA ATOMIC ENERGY RESEARCH INSTITUTE, Daejeon (KR)

( * ) Notice: Subject to any disclaimer, the term of this patent is extended or adjusted under 35 U.S.C. 154(b) by 245 days.

(21) Appl. No.: 15/098,096

(22) Filed: Apr. 13, 2016

(65) Prior Publication Data

US 2016/0354406 A1    Dec. 8, 2016

(30) Foreign Application Priority Data

Apr. 15, 2015  (KR) .................. 10-2015-0053058

(51) Int. Cl.
| | | |
|---|---|---|
| A61K 35/74 | (2015.01) | |
| A61K 41/00 | (2006.01) | |
| A61K 31/717 | (2006.01) | |
| C07H 1/00 | (2006.01) | |
| C07H 3/00 | (2006.01) | |
| C08B 37/00 | (2006.01) | |

(52) U.S. Cl.
CPC ............ *A61K 31/717* (2013.01); *A61K 35/74* (2013.01); *A61K 41/0019* (2013.01)

(58) Field of Classification Search
CPC ... A61K 31/717; A61K 35/74; A61K 41/0019
See application file for complete search history.

(56) References Cited

U.S. PATENT DOCUMENTS

| | | |
|---|---|---|
| 9,090,713 B2 | 7/2015 | Czaja et al. |
| 9,670,289 B2 * | 6/2017 | Czaja ................... C08B 15/02 |
| 2015/0266978 A1 | 9/2015 | Czaja et al. |

FOREIGN PATENT DOCUMENTS

| | | |
|---|---|---|
| KR | 10-2014-0129234 | 11/2014 |
| WO | WO 2013/126635 A1 | 8/2013 |

OTHER PUBLICATIONS

Novaes, Jr., et al., Gengiflex, an Alkali-Cellulose Membrane for GTR [Guided Tissue Regeneration]: Histological Observations,: Brazil Dental Journal, 4(2), 65-71 (1993).*
Colvin and Leppard "The biosynthesis of cellulose by *Acetobacter xylinum* and *Acetobacter acetigenus*" *Canadian Journal of Microbiology* 23:701-707 (1977).
Yamanaka et al. "The structure and mechanical properties of sheets prepared from bacterial cellulose" *Journal of Materials Science* 24:3141-3145 (1989).
D. Byrom "5 Microbial cellulose" *Biomaterials* 265-283 (1991).
Kohavi et al. "Surgically modeled reduced ridge in the beagle dog" *Clinical Oral Implants Research* 2:145-150 (1991).
Ross et al. "Cellulose Biosynthesis and Function in Bacteria" *Microbiological Reviews* 55(1):35-58 (1991).
Jonas and Farah "Production and application of microbial cellulose" *Polymer Degradation and Stability* 59:101-106 (1998).
Ko et al. "Acetobacter Xylinum GS11" *Korean Journal of Microbiology and Biotechnology* 30(1):57-62 (2002).
Shah and Brown "Towards electronic paper displays made from microbial cellulose" *Applied Microbiology and Biotechnology* 66:352-355 (2005).
Chmielewski et al. "Chemical-radiation degradation of natural oligoamino-polysaccharides for agricultural application" *Radiation Physics and Chemistry* 76:1840-1842 (2007).
An et al. "Tissue engineering application of biomimetic bacterial cellulose by gamma-irradiation" *Chonbuk National University* (2014) abstract.

* cited by examiner

*Primary Examiner* — Lawrence E Crane
(74) *Attorney, Agent, or Firm* — Klarquist Sparkman, LLP

(57) ABSTRACT

An absorbable periodontal tissue and bone regeneration material uses bacterial cellulose that has been exposed to radiation. The bacterial cellulose was confirmed to block the invasion of soft tissue in a calvarial defect in rat and rabbit models and to display excellent absorptiveness enough to contribute bone formation. Therefore, the bacterial cellulose can be developed as an absorbable periodontal tissue and bone regeneration material useful in the field of medical engineering by regulating biodegradability without using chemicals that are toxic to human and environment.

7 Claims, 26 Drawing Sheets

[Figure 1]
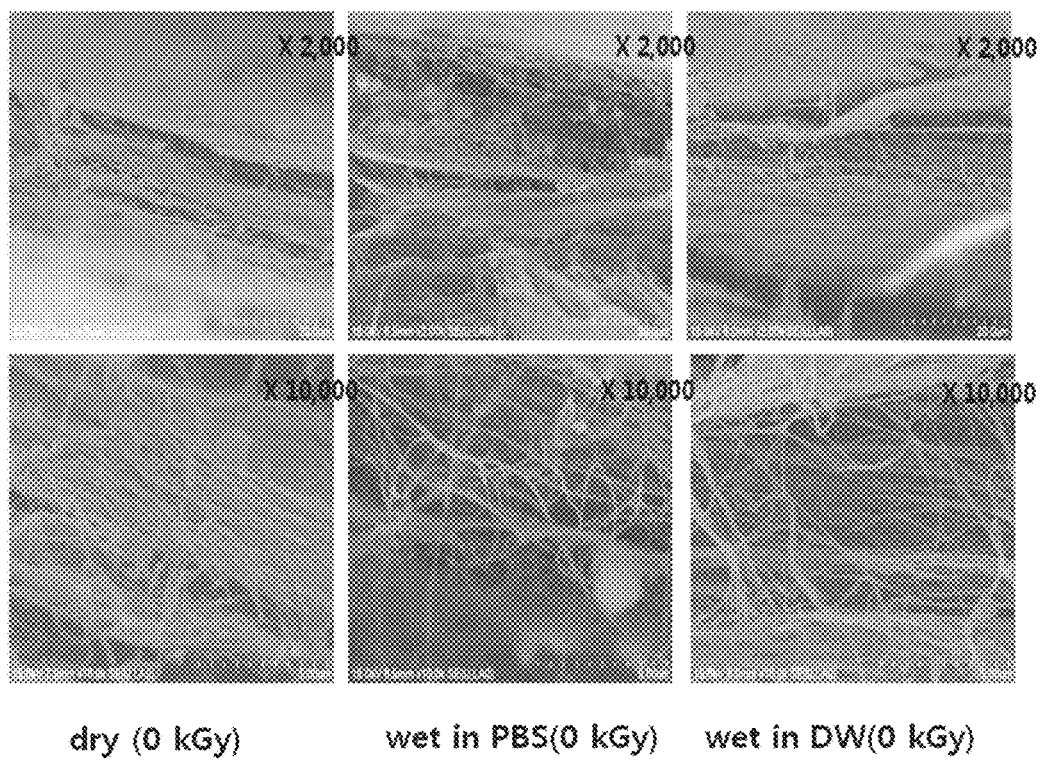

[Figure 2]
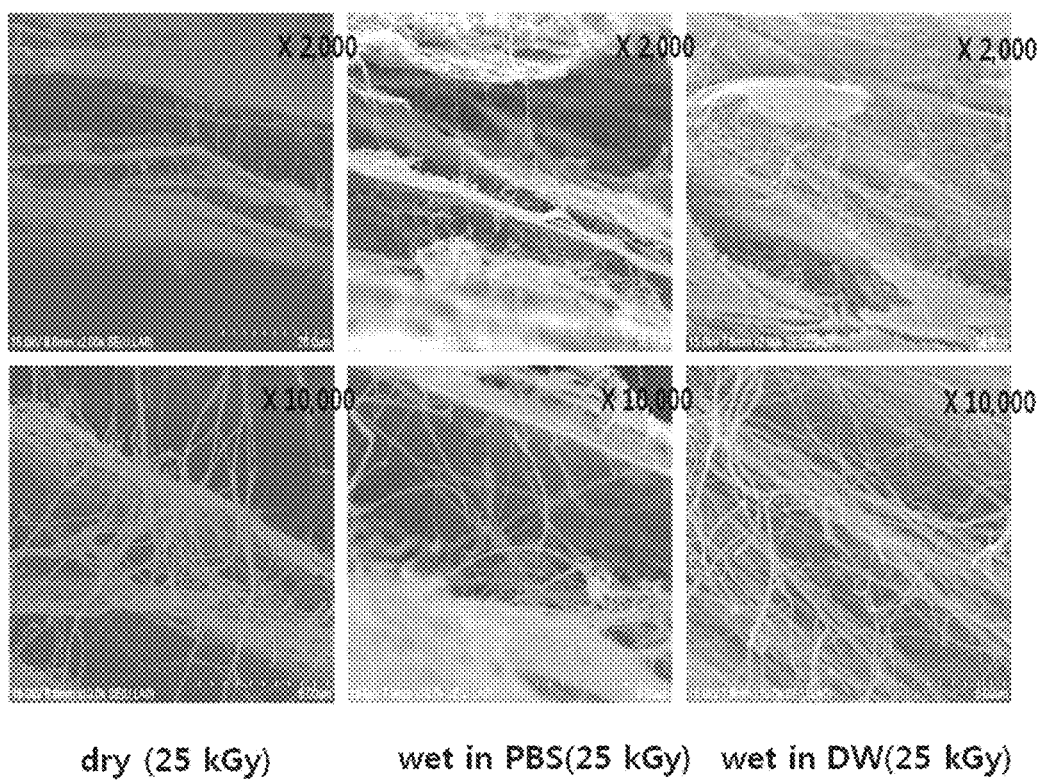
dry (25 kGy)   wet in PBS(25 kGy)   wet in DW(25 kGy)

[Figure 3]
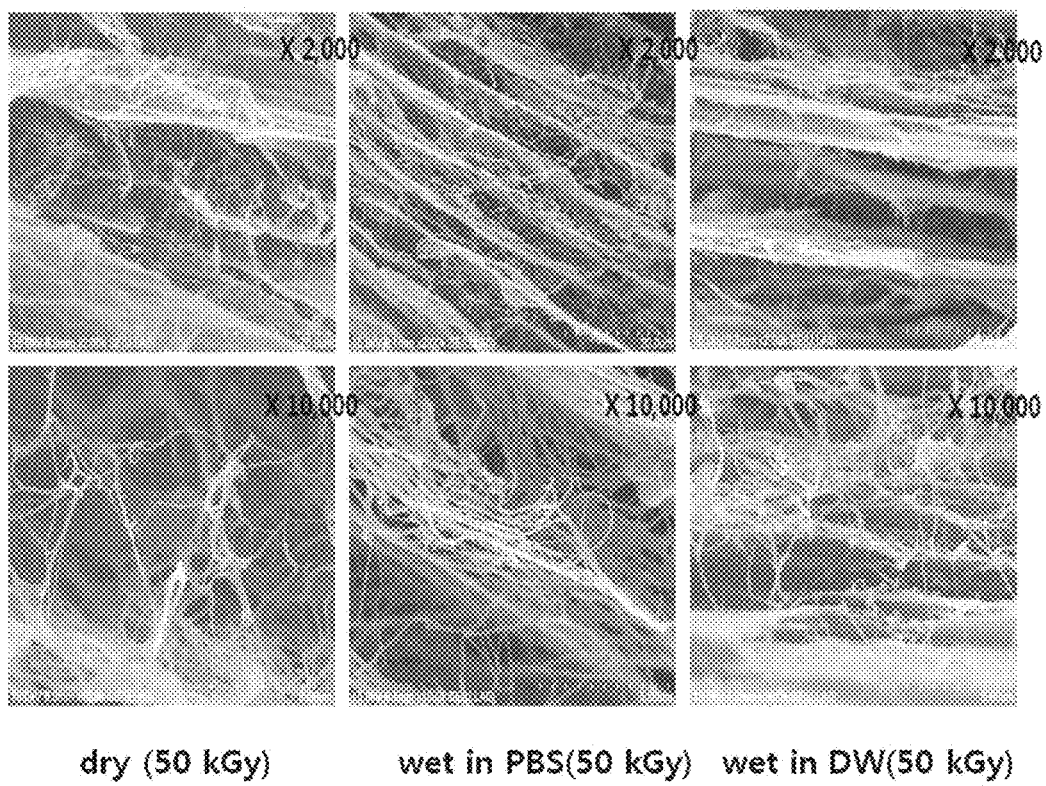

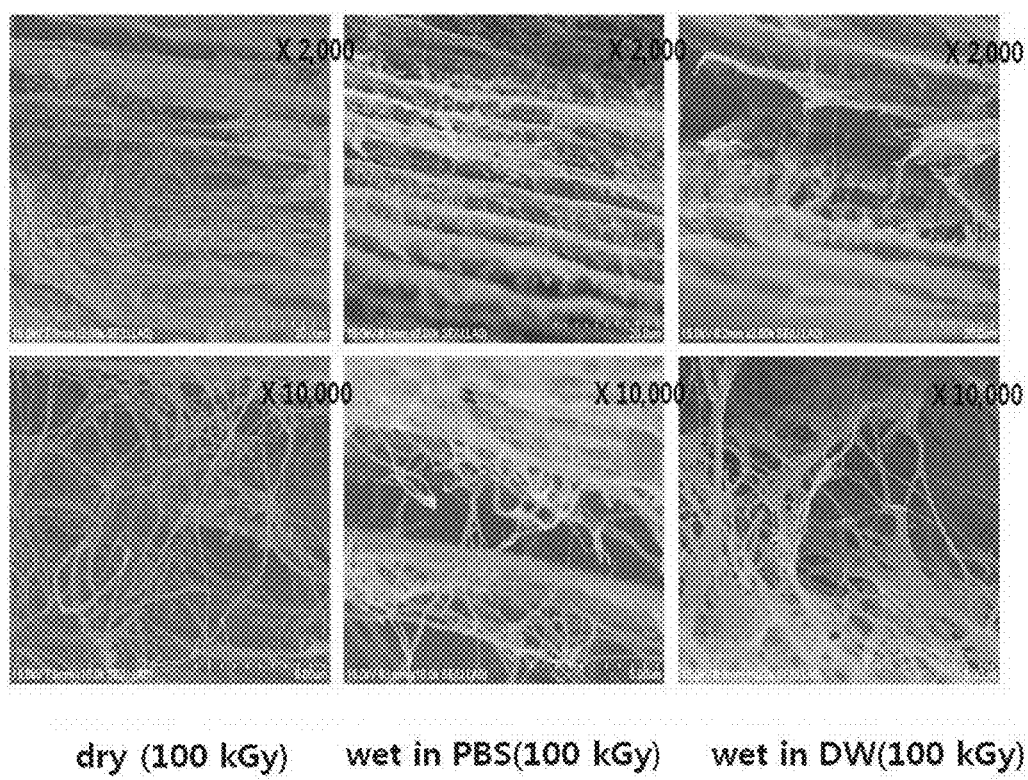
[Figure 4]
dry (100 kGy)   wet in PBS(100 kGy)   wet in DW(100 kGy)

[Figure 5]
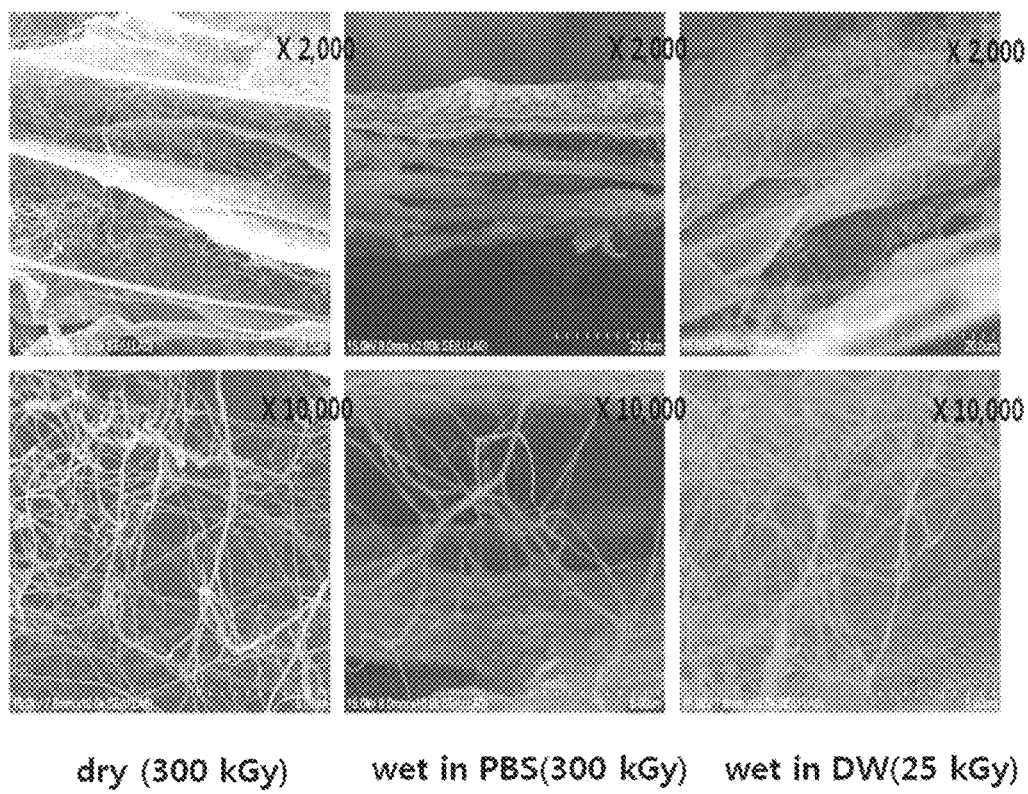
dry (300 kGy)　　wet in PBS(300 kGy)　　wet in DW(25 kGy)

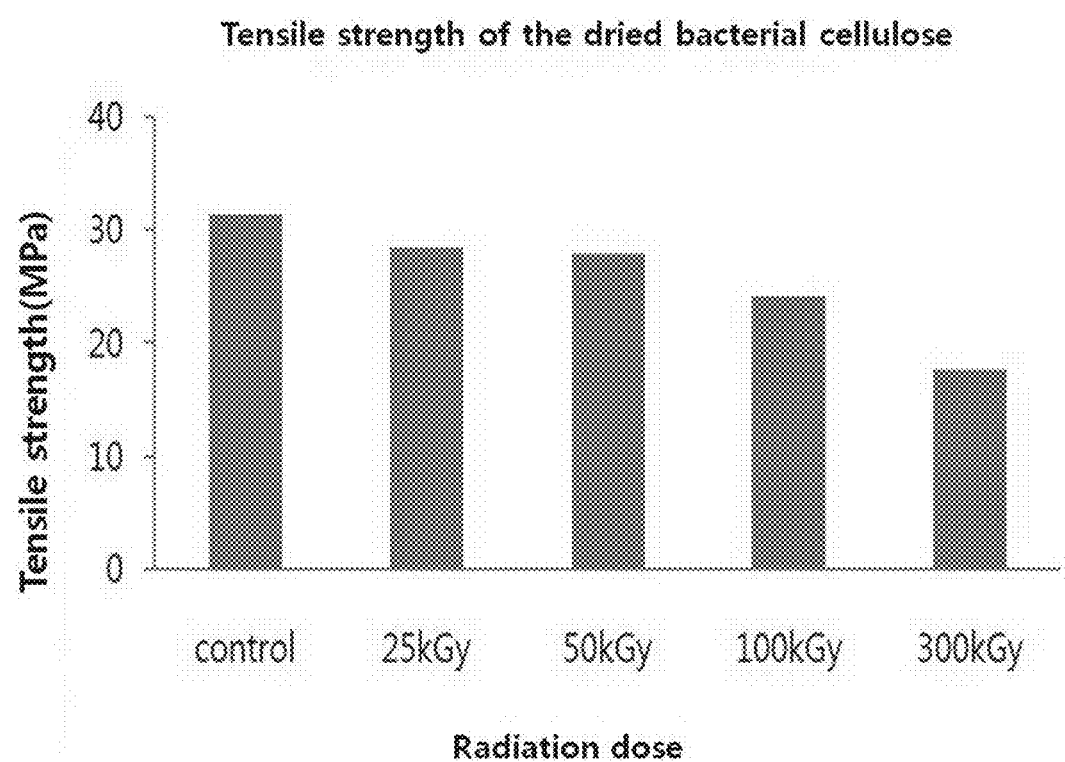
[Figure 6]

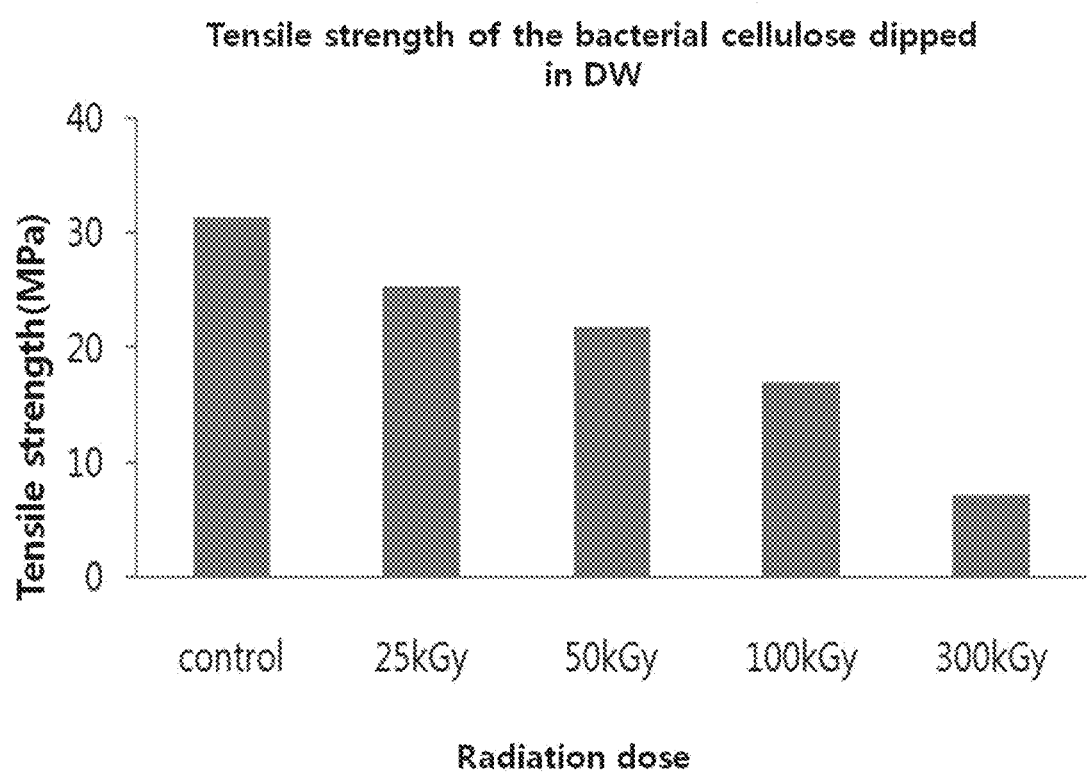

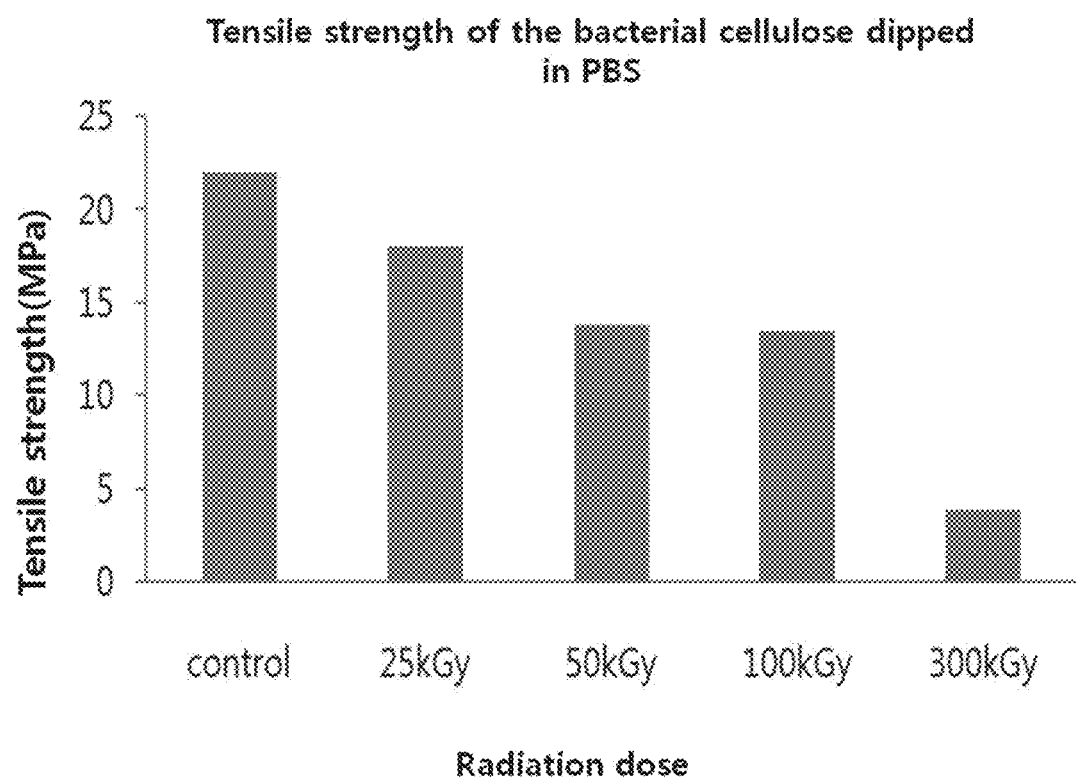

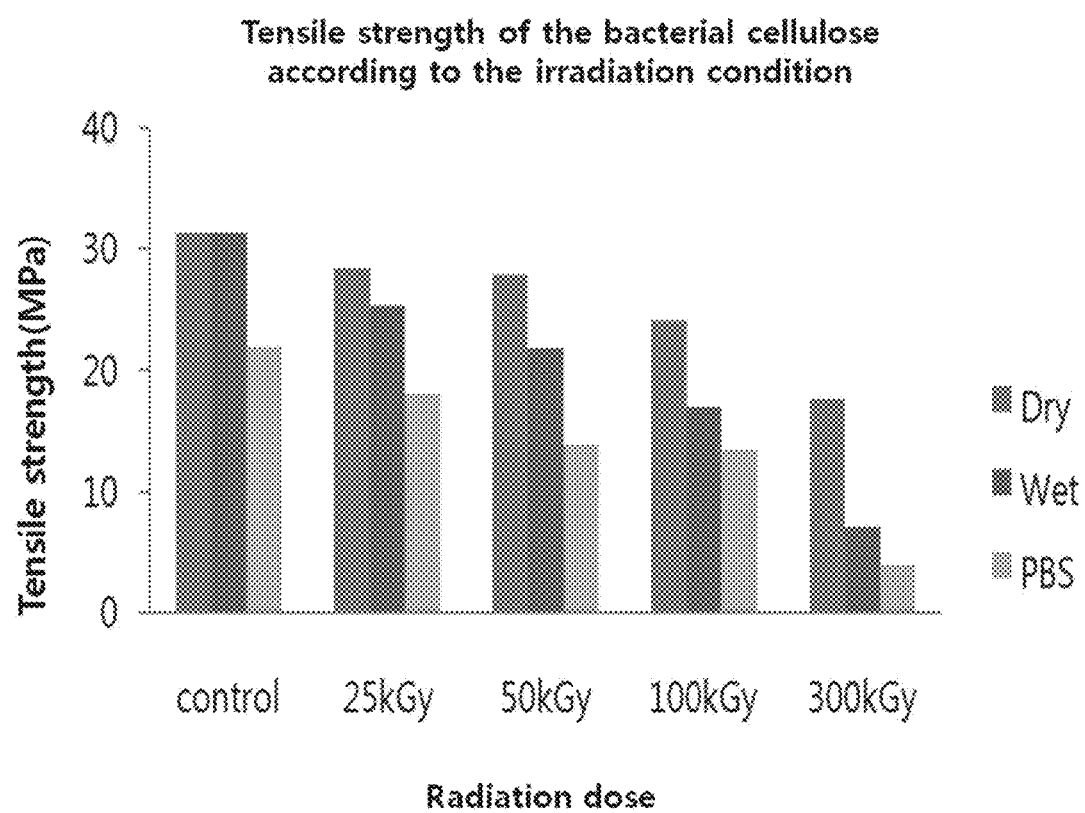
[Figure 9]

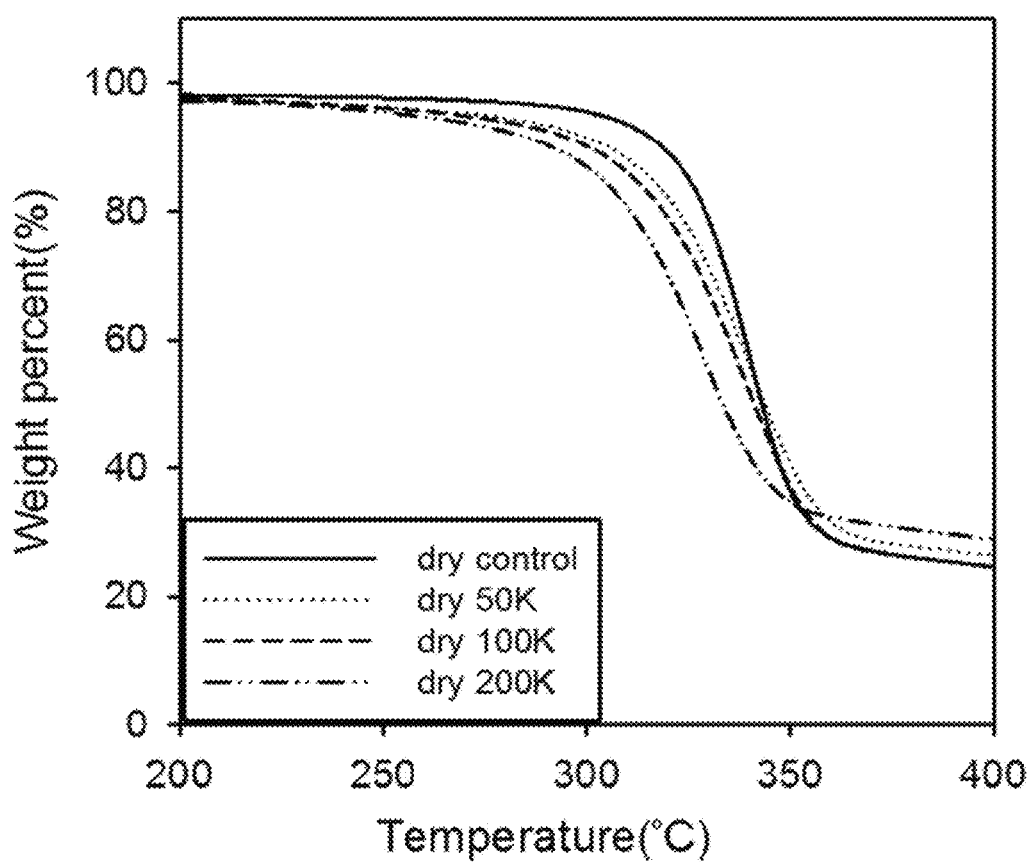
[Figure 10]

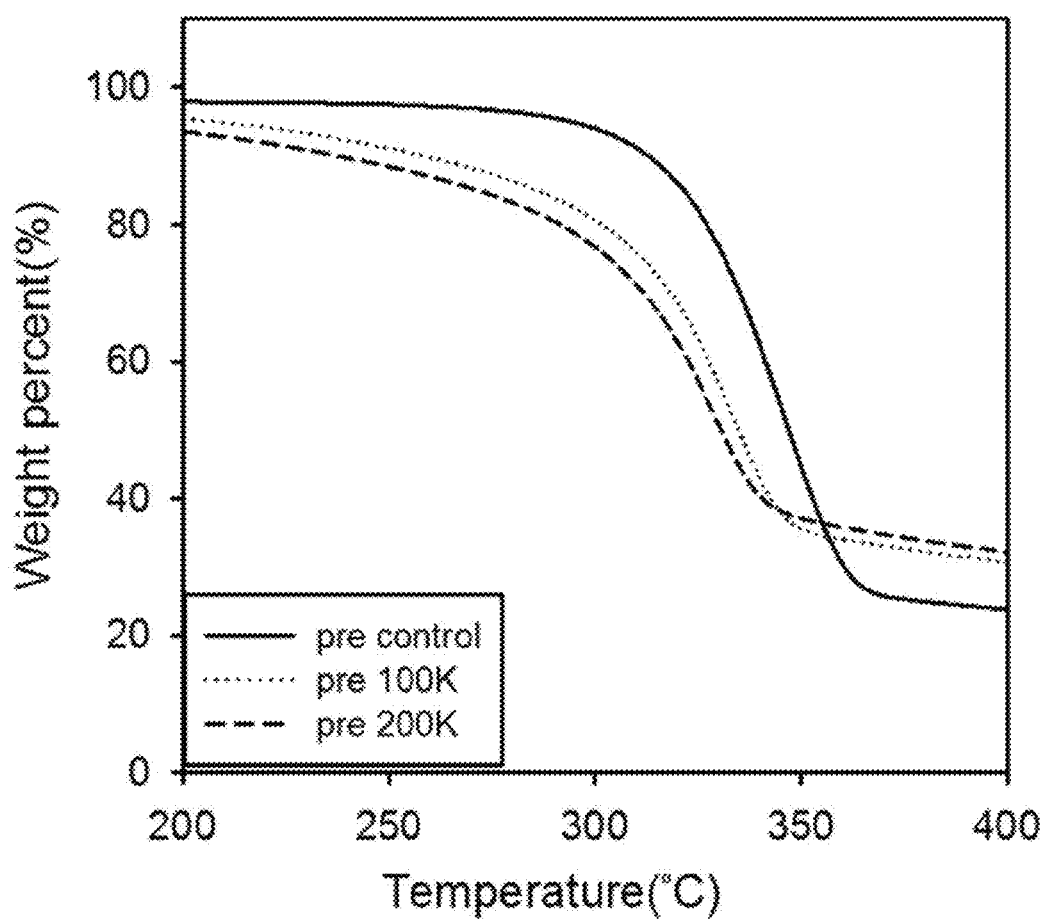
[Figure 11]

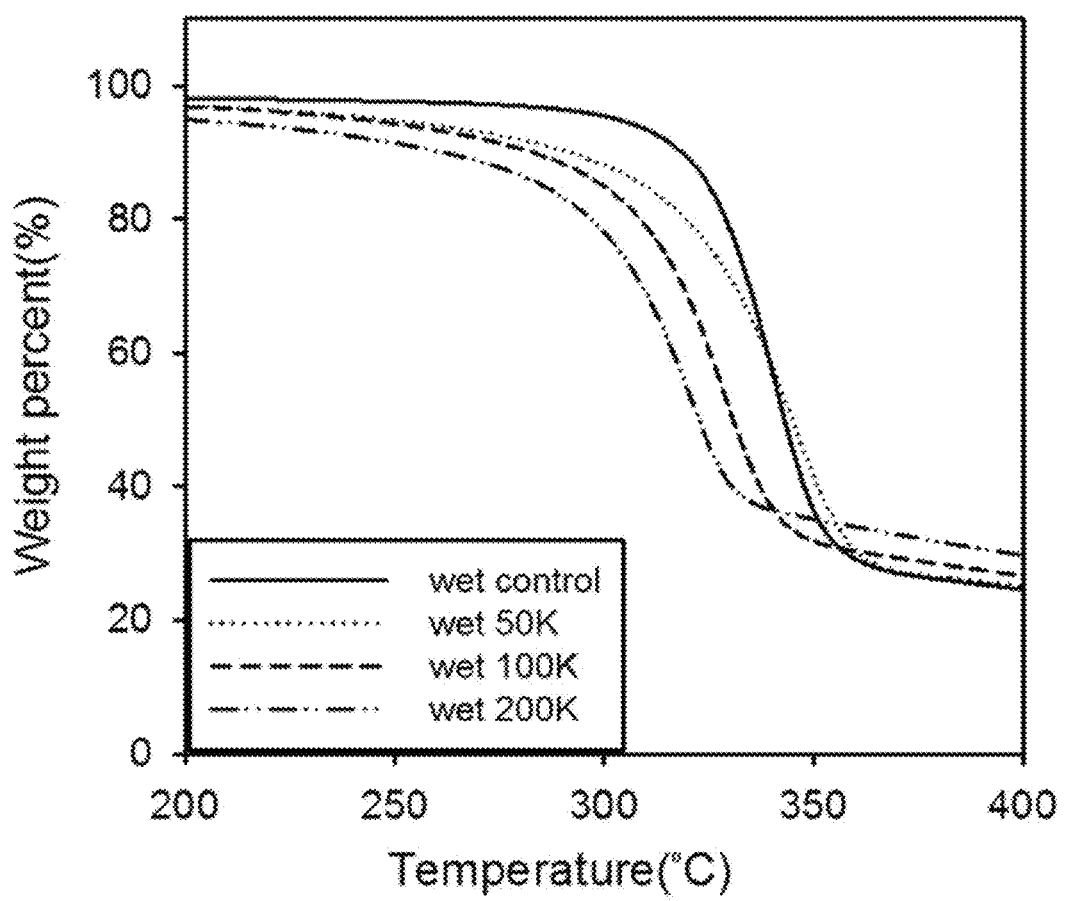
[Figure 12]

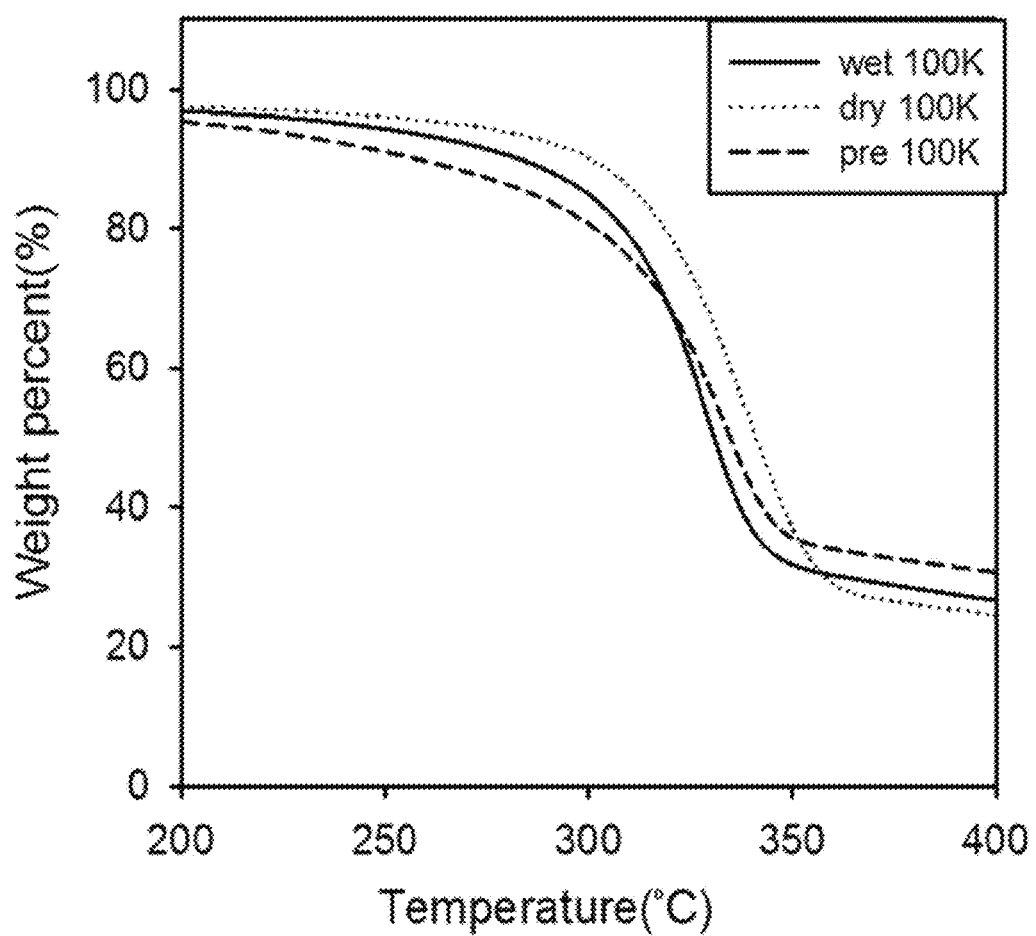
[Figure 13]

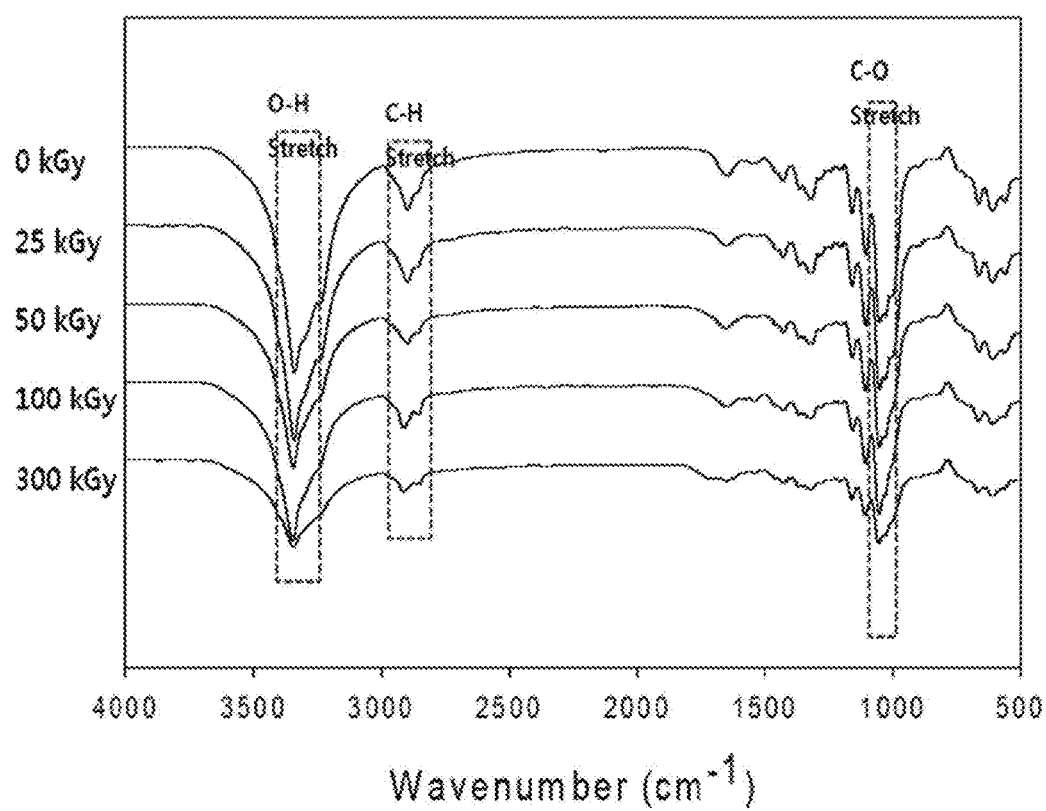
[Figure 14]

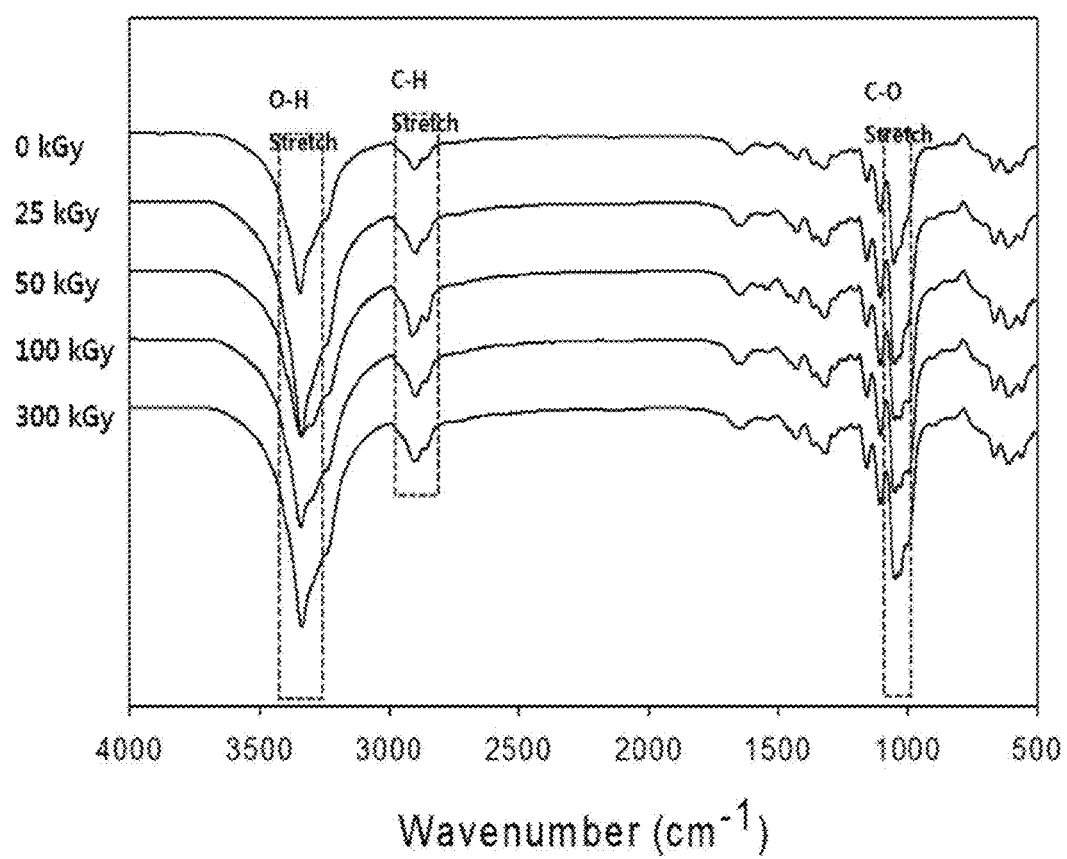
[Figure 15]

[Figure 16]
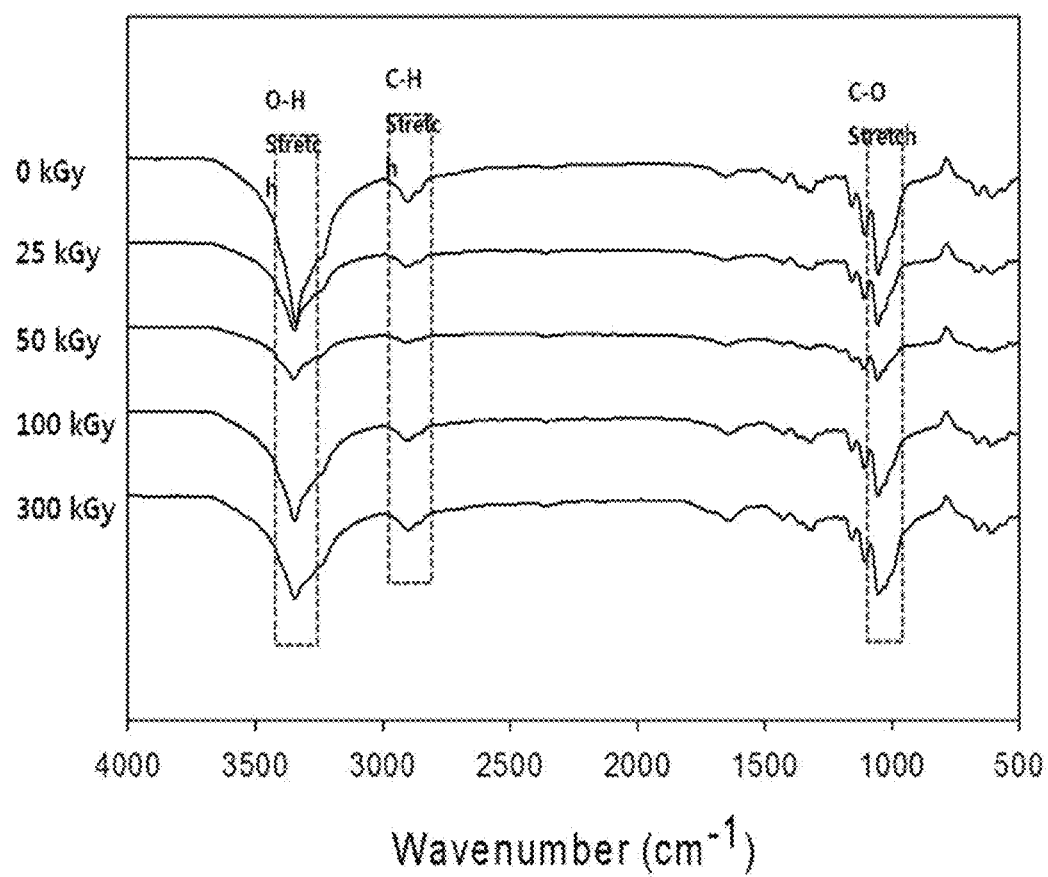

[Figure 17]
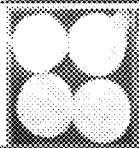

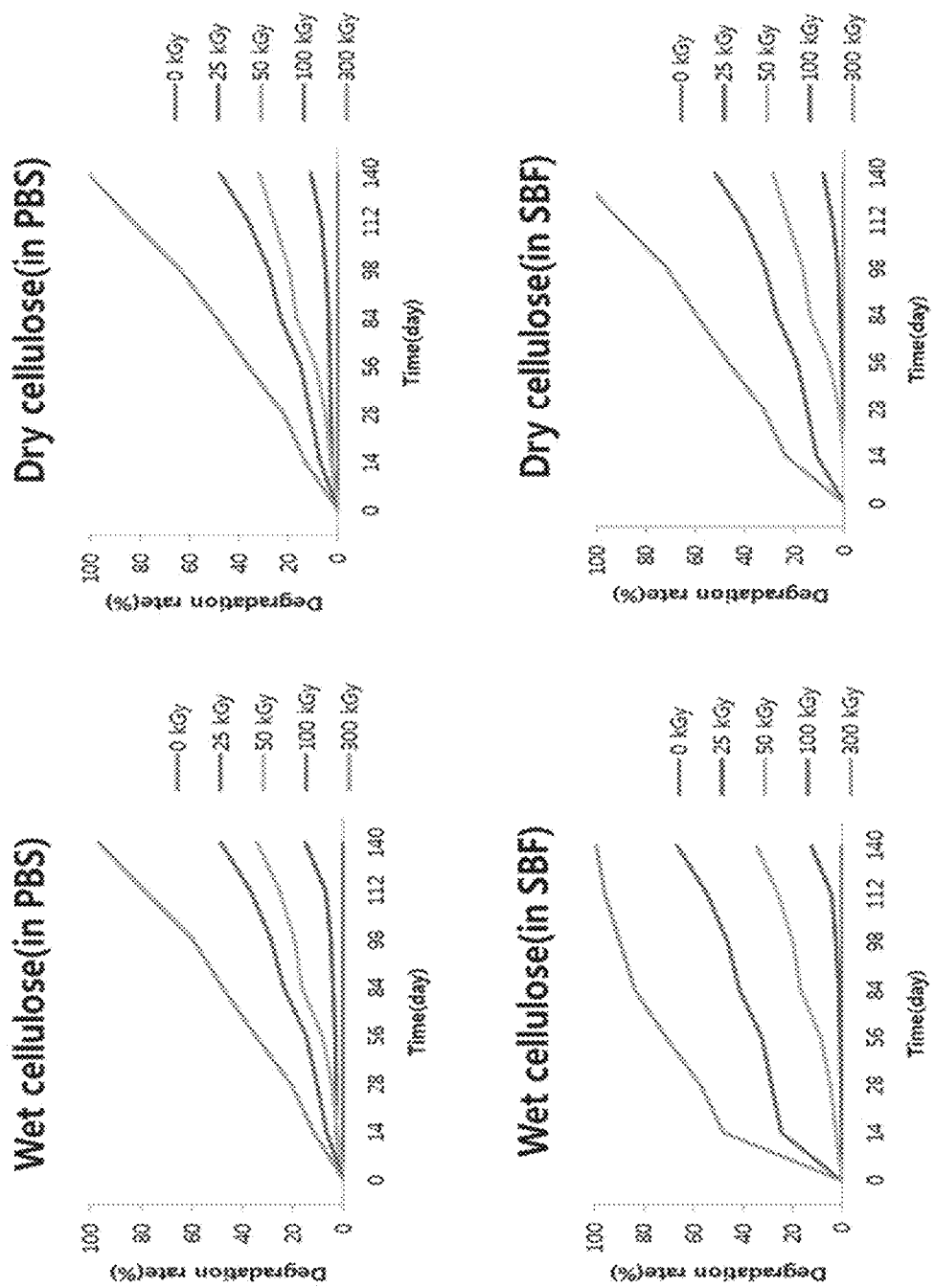
[Figure 18]

[Figure 19]
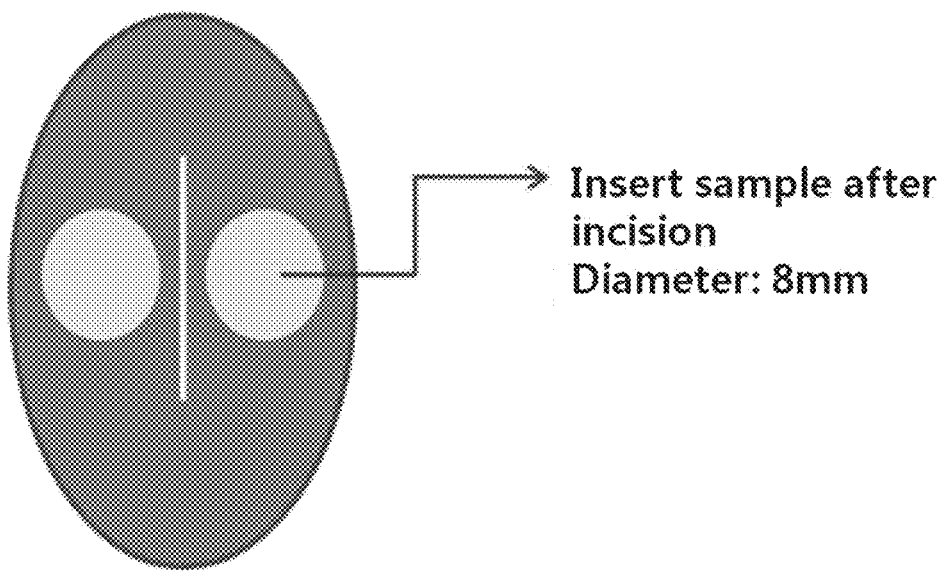

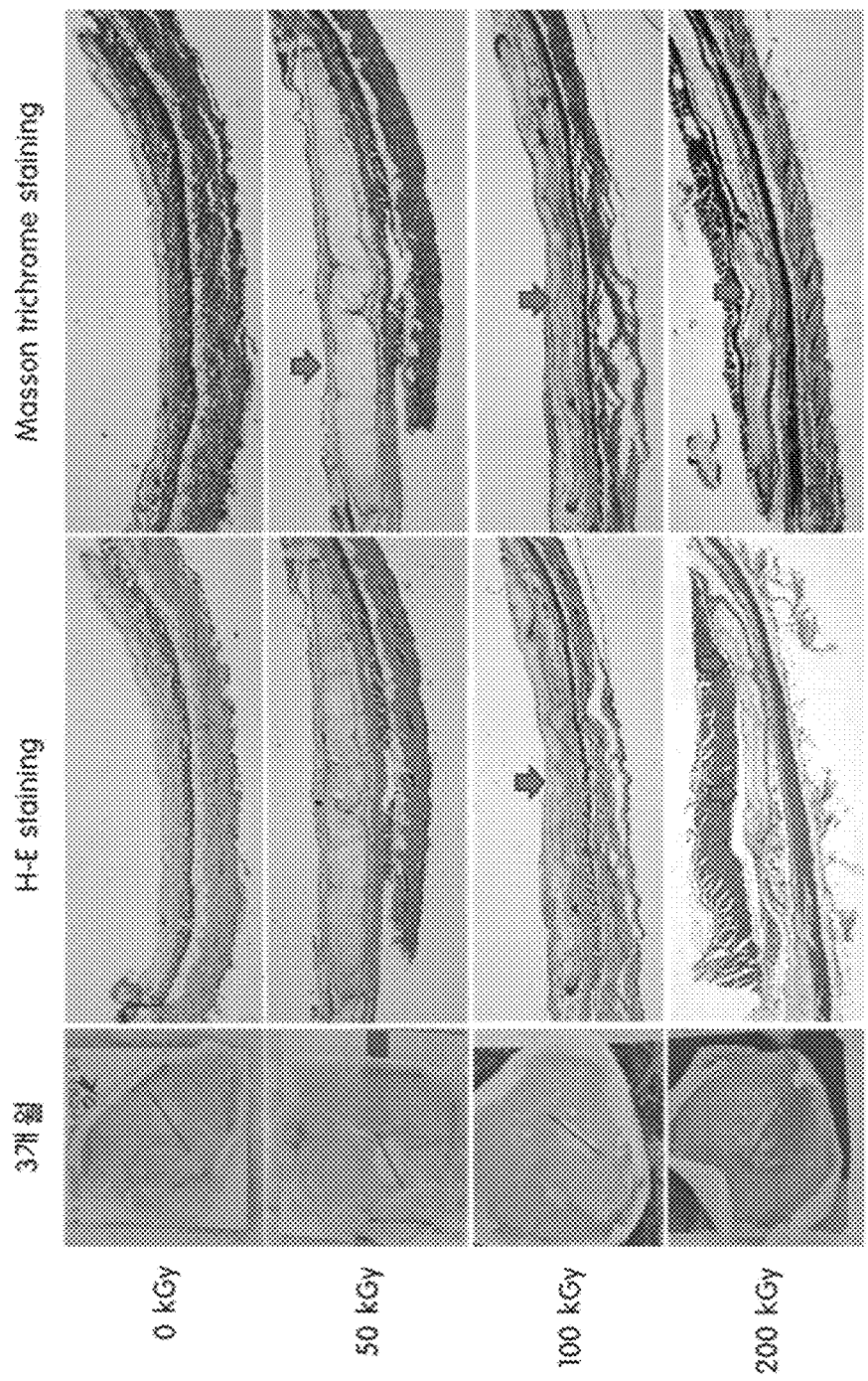
[Figure 20]

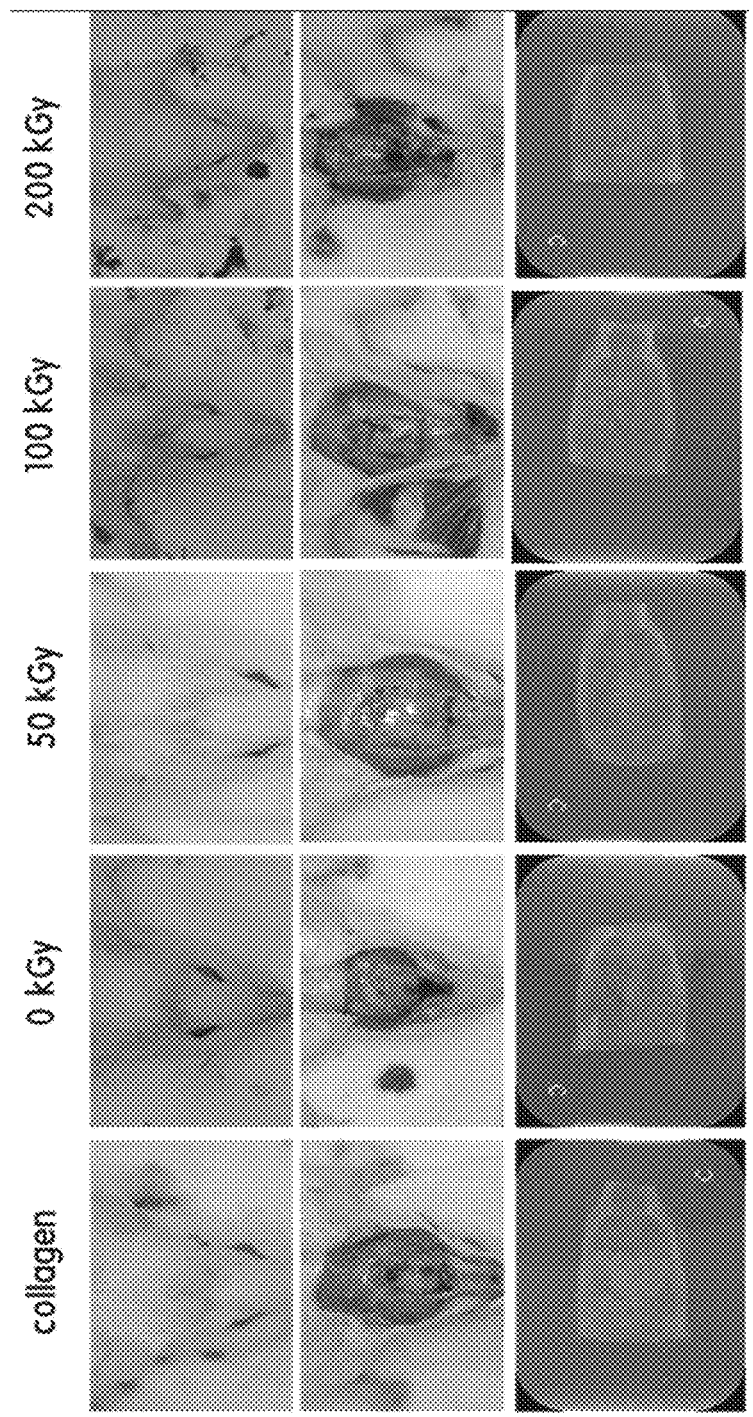
[Figure 21]

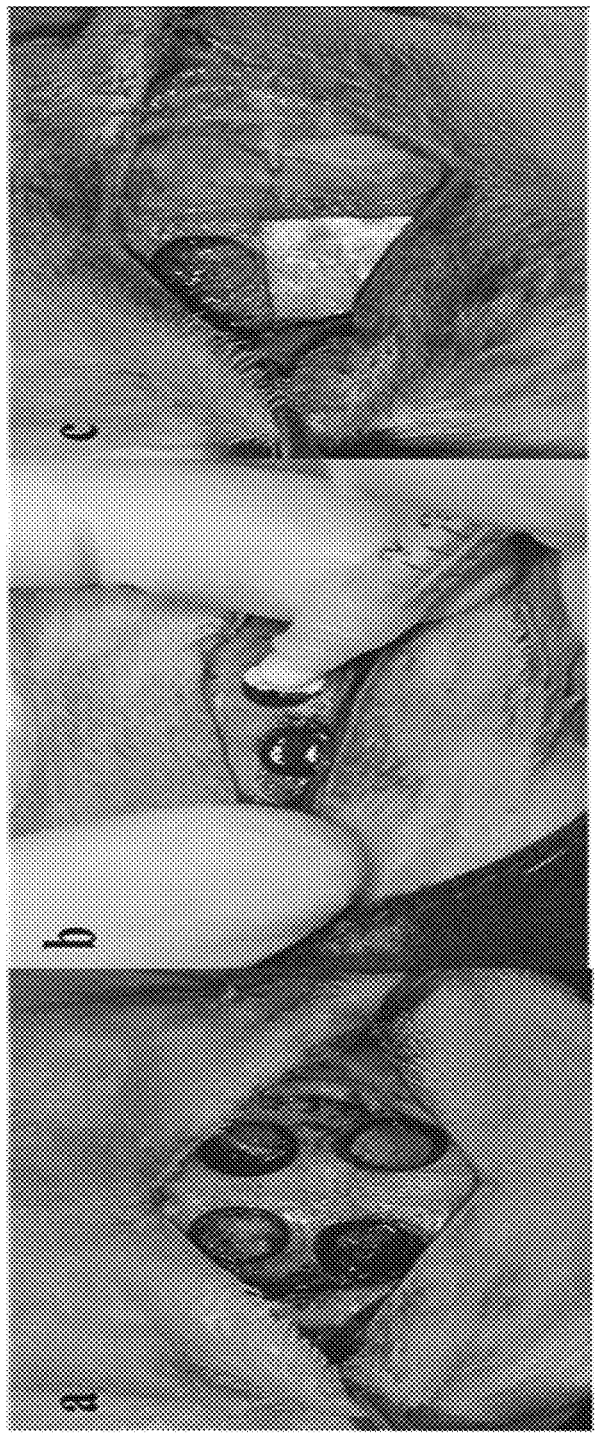
[Figure 22]

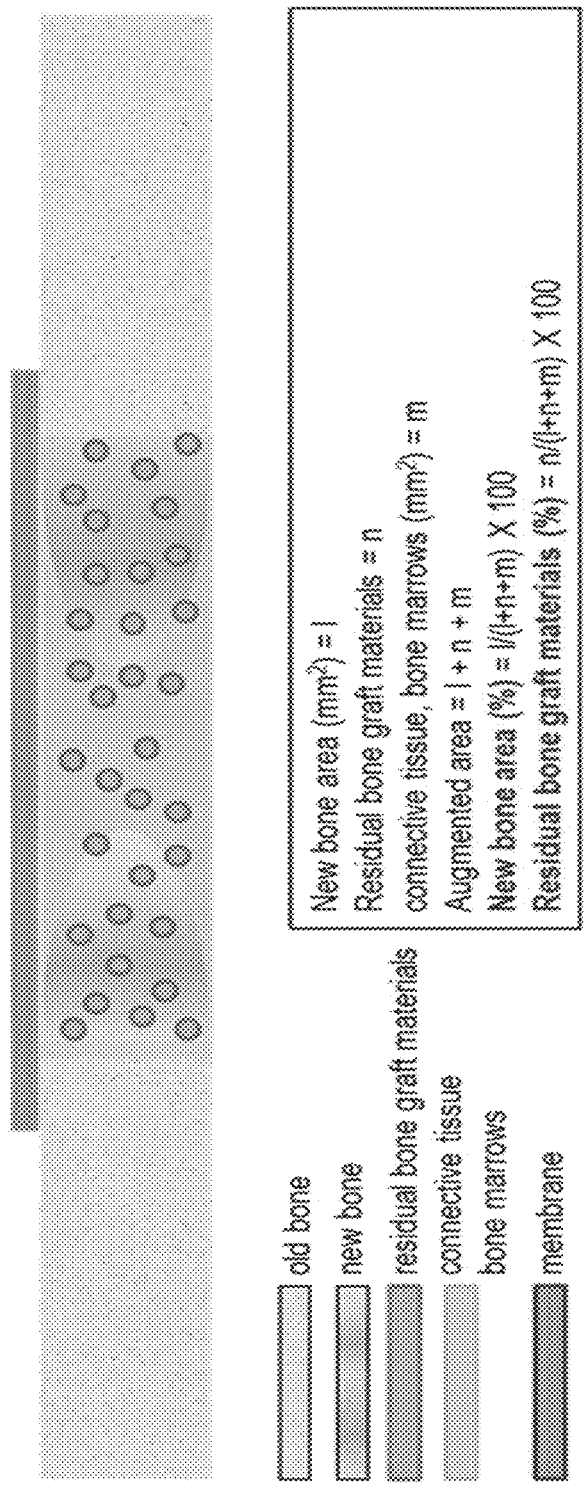
[Figure 23]

[Figure 24]
MicroCT image: Yellow(Control), Blue(100kGy), Red(200kGy)

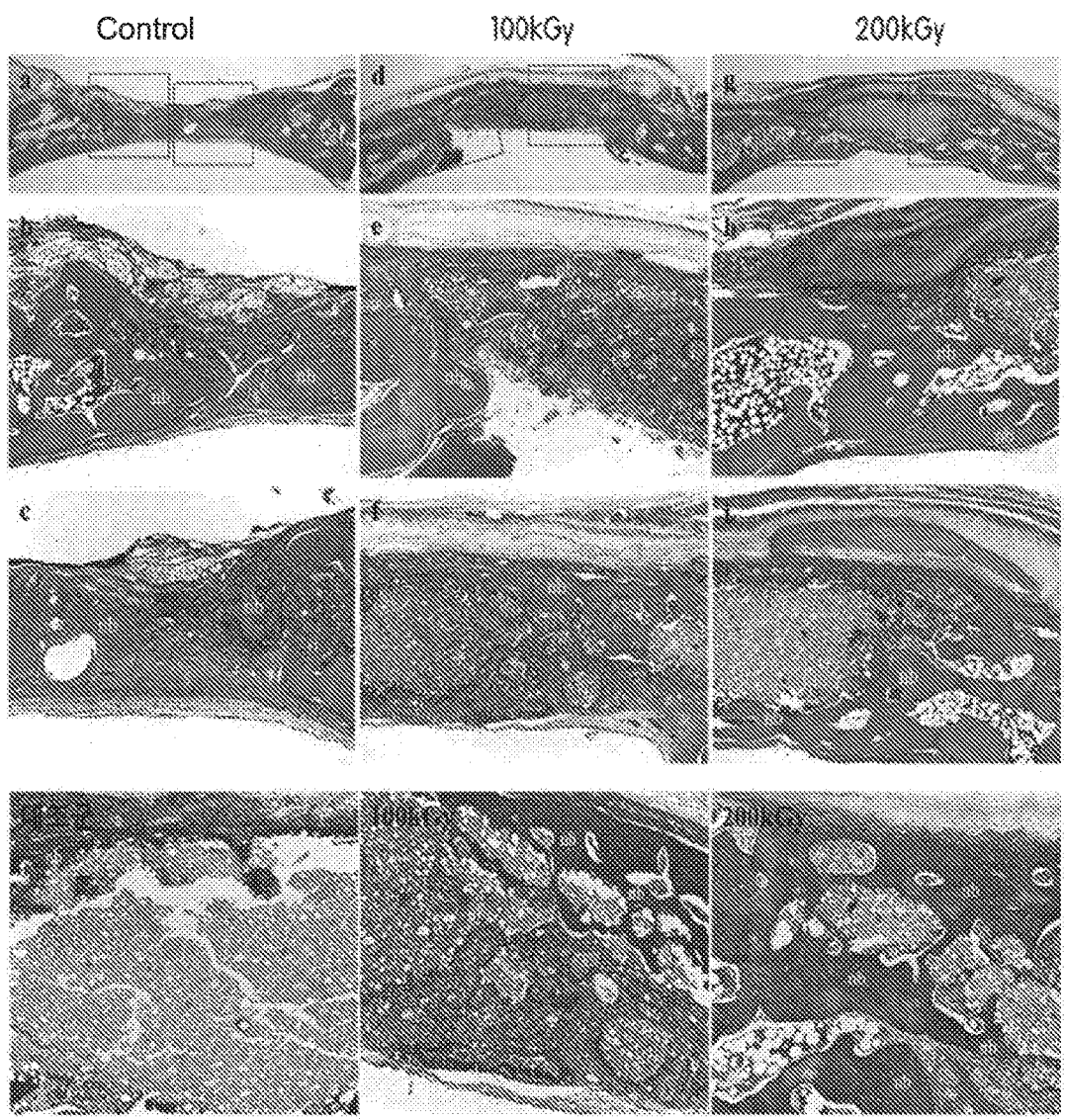
[Figure 25]

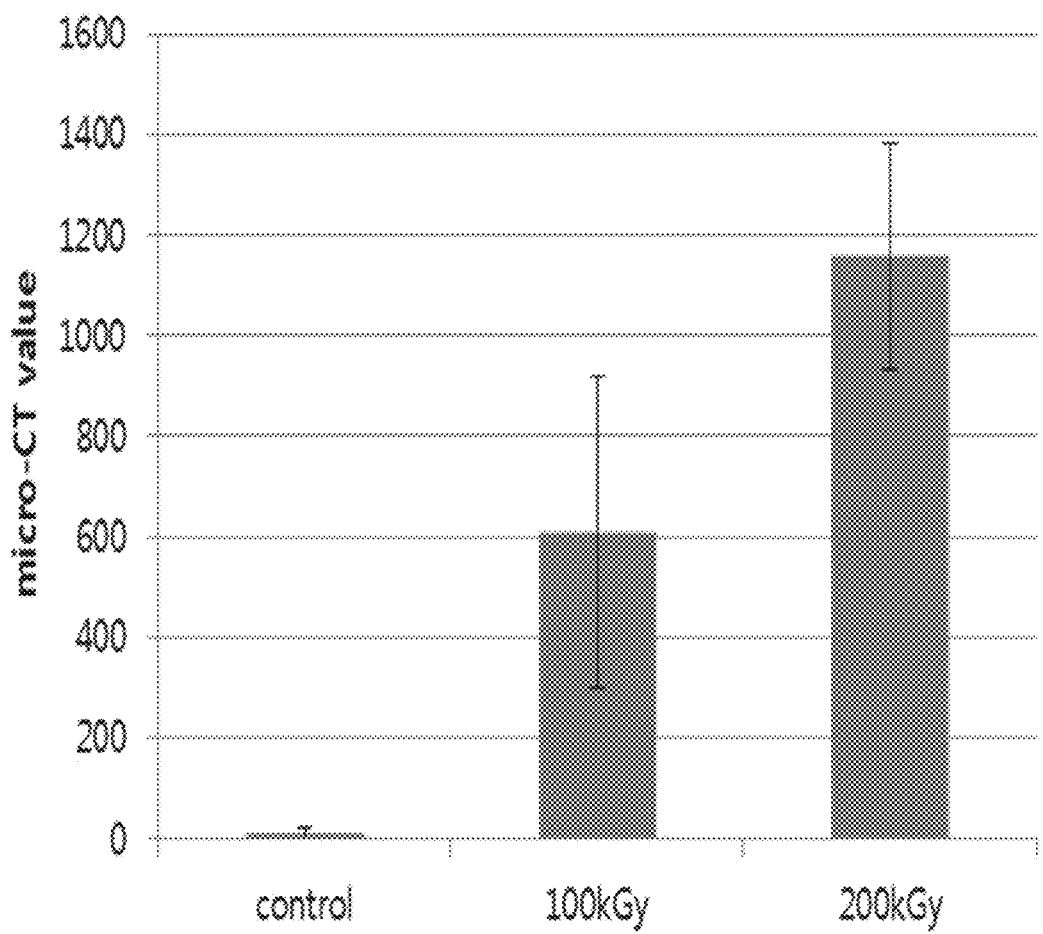

BIODEGRADABLE CONTROL OF BACTERIAL CELLULOSE BY RADIATION TECHNOLOGY AND ABSORBABLE PERIODONTAL MATERIAL USING SAME

CROSS REFERENCE TO RELATED APPLICATION

This application claims priority under the Paris Convention to Republic of Korea Application 10-2015-0053058, filed Apr. 15, 2015.

BACKGROUND OF THE INVENTION

1. Field of the Invention

The present invention relates to the biodegradable control of bacterial cellulose by radiation technology and an absorbable periodontal tissue and bone regeneration material using the same.

2. Description of the Related Art

Cellulose is a renewable and the most abundant resource in the natural world, which is a polysaccharide composed of glucose in β-1,4 linkage. Cellulose is not only used in various industrial fields including paper and pulp industry but also applied to a variety of industrial fields. Thus, the consumption of cellulose is increasing significantly. Cellulose has a strong resistance against chemicals and microorganism attack, so that it is used as a raw material for the production of paper and clothes. Ether derivative is used as a raw material of rayon and nitroester is used as a raw material of gunpowder (non-patent reference 1-3).

The generation of cellulose is mainly accomplished in plants but is possibly achieved in bacteria. A general plant fiber is composed of cellulose, hemicellulose, and lignin. In the meantime, the bacterial cellulose is composed of only pure cellulose so that it does not need to be purified additionally (non-patent reference 4). According to the previous studies, the major bacterium that can synthesize cellulose is *Acetobacter xylinum*. In addition, numbers of bacteria genera including *Agrobacterium, Pseudomonas, Rhizobium,* and *Sarcina* are known to produce cellulose (non-patent reference 5). It was first reported by Brown in 1886 that cellulose could be produced not only in plants but also in microorganisms such as acetic acid bacteria. The strain that can produce bacterial cellulose with the highest yield is *Acetobacter xylinum* which is gram-negative aerobic microorganism, because of which it has long been a target of study about bacterial cellulose (non-patent reference 6).

The potential of the bacterial cellulose for being applied to a variety of fields, due to its unique physiochemical and mechanical properties, was reported earlier (non-patent reference 4). The most efficient producing strain of bacterial cellulose is the gram negative *Acetobacter xylinum*, more specifically *Gluconacetobacter xylinus* (non-patent reference 7). The strain exists as a single or a couple or in chains, and is reproduced by binary fission, but does not form endospores. In a limited condition, *A. xylinum* displays the degenerated form, which is often found in swollen or extended filament. The proper temperature for the growth of *Acetobacter xylinum* is 25~30° C. and the proper pH is 5.4~6.2.

Unlike the plant-derived cellulose, bacterial cellulose is the pure cellulose that does not include any impurities such as hemicelluloses, pectin, lignin, and biogenic products, so that high purity cellulose can be purified with a small amount of energy and materials (non-patent reference 8). The bacterial cellulose has a three-dimensional network structure formed by hydrogen bonds of nanofibrils (20~50 nm), and has high tensile strength, water retention power, and Young's modulus, so that it can be applied to high-performance diaphragm, high-quality paper, cosmetics, and dietary food, etc. According to the advancement of recent biomedical materials, the bacterial cellulose is also tried in wound dressing and drug delivery systems (DDS) using natural polymers and synthetic polymers. The bacterial cellulose generated by some bacteria is excellent in its physical and biological properties, which favors the application to the field of biomedicine. The bacterial cellulose produced by *Acetobacter xylinum* has been recognized as a high-value product in the field of biotechnology and has been successfully used as burn wound dressing (non-patent reference 9).

The absorbable periodontal tissue regeneration material is to shield the area of periodontal bone regeneration to induce the regeneration of damaged periodontal bone. Collagen was conventionally used as the material. However, a collagen membrane is easily degraded before the regeneration of periodontal bone is completed. In addition to the high price, the collagen membrane cannot guarantee the successful bond formation.

The present inventors succeeded in maintaining the shield effect with the bacterial cellulose until the periodontal tissue and bone were completely regenerated by using radiation technology, precisely by cutting the linkage of cellulose physically to regulate biodegradation so that the biodegradation speed could be slowed compared with the conventional collagen membrane, leading to the completion of the invention which can bring high economic effect as well since the inventors used the low-priced bacterial cellulose.

PRIOR ART REFERENCES

Non-Patent References

1. D Kohavi, S R Pollack, G Brighton, et al., "Surgically modeled reduced ridge in the beagle dog", Clin. Oral. Impl. Res., 2, 145 (1991).
2. D Byrom, "Microbiol cellulose", biomaterials, 236 (1991).
3. Ko, J. Y., K. S. Shin, B. D. Yoon, et al., "Production of bacterial cellulose by *Acetobacter xylimm* GS11", Kor. J. Appl. Microbiol. Biotechnol. 30, 57 (2002).
4. J. Shah and R. Malcolm Brown, "Towards Electronic Paper Displays Made From Microbial Cellulose.", Applied Microbiology and Biotechnology, 66, 352 (2005).
5. Jonas, Rainer and Farah, Luiz F., "Production and application of microbial cellulose.", Polymer Degradation and Stability, 59(1-3), 101 (1998).
6. Ross, P., Mayer, R. Benziman, M. Microbiol. Rev., 55, 35 (1991).
7. J. Colvin and G. Leppard, "The Biosynthesis of Cellulose by *Acetobacter xylinum* and *Acetobacter acetigenus*.", Canadian Journal of Microbiology, 23, 701 (1977).
8. Rainer, J., F. F. Luiz, "Production and application of microbial cellulose. polym". Degrad. stud., 58, 101 (1986).
9. Yamanaka, S., K. Watanabe, N. Kitamura, et al., "The structure and mechanical properties of sheets prepared from bacterial cellulose", J. Mat. Sci., 24, 3141 (1989).
10. Chmielewski A G, W Migdal, J Swietoslawski, J Swietoslawski, U Jakubaszek and T Tarnowski. 2007. Chemical-radiation degradation of natural oligoamino-polysaccharides for agricultural application. Radiat. Phys. Chem. 76:840-1842.

SUMMARY

It is an object of the present disclosure to provide a method for the biodegradable control of bacterial cellulose using radiation technology and provide an absorbable periodontal tissue and bone regeneration material using the same.

To achieve the above object, the present invention provides a periodontal tissue or bone regeneration material comprising irradiated bacterial cellulose as an active ingredient.

The present invention also provides a barrier membrane for the inducement of absorbable periodontal tissue or bone regeneration comprising the irradiated bacterial cellulose as an active ingredient.

The present invention also provides a support for the regeneration of absorbable periodontal tissue or bone comprising the irradiated bacterial cellulose as an active ingredient.

The present invention also provides a method for the preparation of an absorbable periodontal tissue or bone regeneration material comprising the following steps:
1) pre-treating the bacterial cellulose; and
2) irradiating the pre-treated bacterial cellulose of step 1) with radiation.

In addition, the present disclosure provides a method for inhibiting the biodegradability of the bacterial cellulose and a method for increasing the flexibility and absorptiveness of the same comprising the following steps:
1) pre-treating the bacterial cellulose; and
2) irradiating the pre-treated bacterial cellulose of step 1) with radiation.

Advantageous Effect

The present invention relates to an absorbable periodontal tissue and bone regeneration material using the bacterial cellulose based on the radiation technology. The bacterial cellulose exposed to the radiation was confirmed to block the invasion of soft tissue in the calvarial defect of rat and rabbit models and to display excellent absorptiveness enough to contribute bone formation. Therefore, the said bacterial cellulose of the invention can be developed as an absorbable periodontal tissue and bone regeneration material necessary in the field of medical engineering by regulating biodegradability using the radiation technology without using chemicals which are toxic to human and environment.

BRIEF DESCRIPTION OF THE DRAWINGS

The application of the preferred embodiments of the present invention is best understood with reference to the accompanying drawings, wherein:

FIG. 1 is a diagram illustrating the result of microstructure analysis (SEM) of the bacterial cellulose according to the radiation dose (0 kGy) and irradiation condition (dry, wet in distilled water (DW), and wet in PBS).

FIG. 2 is a diagram illustrating the result of microstructure analysis (SEM) of the bacterial cellulose according to the radiation dose (25 kGy) and irradiation condition (dry, wet in distilled water (DW), and wet in PBS).

FIG. 3 is a diagram illustrating the result of microstructure analysis (SEM) of the bacterial cellulose according to the radiation dose (50 kGy) and irradiation condition (dry, wet in distilled water (DW), and wet in PBS).

FIG. 4 is a diagram illustrating the result of microstructure analysis (SEM) of the bacterial cellulose according to the radiation dose (100 kGy) and irradiation condition (dry, wet in distilled water (DW), and wet in PBS).

FIG. 5 is a diagram illustrating the result of microstructure analysis (SEM) of the bacterial cellulose according to the radiation dose (300 kGy) and irradiation condition (dry, wet in distilled water (DW), and wet in PBS).

FIG. 6 is a diagram illustrating the tensile strength of the dried bacterial cellulose according to the radiation dose (0, 25, 50, 100, and 300 kGy).

FIG. 7 is a diagram illustrating the tensile strength of the bacterial cellulose dipped in distilled water according to the radiation dose (0, 25, 50, 100, and 300 kGy).

FIG. 8 is a diagram illustrating the tensile strength of the bacterial cellulose dipped in PBS according to the radiation dose (0, 25, 50, 100, and 300 kGy).

FIG. 9 is a diagram illustrating the tensile strength of the bacterial cellulose according to the radiation dose (0, 25, 50, 100, and 300 kGy) and the condition (dry, wet in distilled water (DW), and wet in PBS):
Dry: dried bacterial cellulose;
Wet: bacterial cellulose dipped in distilled water; and
PBS: bacterial cellulose dipped in PBS.

FIG. 10 is a diagram illustrating the result of thermogravimetry of the dried bacterial cellulose according to the radiation dose (0, 50, 100, and 200 kGy).

FIG. 11 is a diagram illustrating the result of thermogravimetry of the bacterial cellulose dipped in PBS according to the radiation dose (0, 50, 100, and 200 kGy).

FIG. 12 is a diagram illustrating the result of thermogravimetry of the bacterial cellulose dipped in distilled water according to the radiation dose (0, 50, 100, and 200 kGy).

FIG. 13 is a diagram illustrating the result of thermogravimetry of the bacterial cellulose irradiated with radiation at 100 kGy according to the conditions:
wet: bacterial cellulose dipped in distilled water when irradiated with radiation;
dry: dried bacterial cellulose irradiated with radiation; and
pre bacterial cellulose wet in PBS when irradiated with radiation.

FIG. 14 is a diagram illustrating the result of ATR-FTIR to analyze the surface characteristics of the dried bacterial cellulose according to the radiation dose.

FIG. 15 is a diagram illustrating the result of ATR-FTIR to analyze the surface characteristics of the bacterial cellulose wet in distilled water according to the radiation dose.

FIG. 16 is a diagram illustrating the result of ATR-FTIR to analyze the surface characteristics of the bacterial cellulose wet in PBS according to the radiation dose.

FIG. 17 is a diagram illustrating the in vitro degradation of the bacterial cellulose wet in PBS when irradiated with radiation, observed with the naked eye.

FIG. 18 is a diagram presenting the in vitro degradation of the bacterial cellulose wet in PBS and SBF when irradiated with radiation.

FIG. 19 is a diagram illustrating the method of animal transplantation for the investigation of the in vivo degradation of the bacterial cellulose irradiated with radiation.

FIG. 20 is a diagram illustrating the result of histological staining presenting the in vivo absorption of the bacterial cellulose in a test rat 3 months after the transplantation, according to the radiation dose.

FIG. 21 is a diagram illustrating the observation of the calvarial defected rat model transplanted with the bacterial cellulose after the treatment of collagen, the control, according to the radiation dose.

FIG. 22 is a diagram illustrating the process of calvarial defection for the transplantation of the bacterial cellulose of the invention in a rabbit.

FIG. 23 is a schematic diagram illustrating the result of histometric analysis of the calvarial defected rabbit model transplanted with the bacterial cellulose of the invention:

FIG. 24 is a diagram illustrating the result of micro CT of the calvarial defected rabbit model to detect any changes according to the radiation dose, performed 4 weeks after the transplantation of the bacterial cellulose.

FIG. 25 is a diagram illustrating the result of histological staining presenting the in vivo absorption of the bacterial cellulose in the calvarial defected rabbit 4 weeks after the transplantation, according to the radiation dose.

FIG. 26 is a diagram illustrating the result of micro CT for the investigation of the in vivo absorption of the bacterial cellulose according to the radiation dose in the calvarial defected rabbit transplanted with the bacterial cellulose.

DESCRIPTION OF THE PREFERRED EMBODIMENTS

Hereinafter, the preferred embodiments are described in detail.

A periodontal tissue or bone regeneration material comprises bacterial cellulose as an active ingredient, wherein the bacterial cellulose has been irradiated with radiation.

The radiation herein is preferably selected from the group consisting of gamma-ray, electron beam, x-ray, and ultraviolet (UV) rays, and more preferably electron beam, but not always limited thereto.

The radiation dose is preferably 100~300 kGy, and more preferably 150~250 kGy, but not always limited thereto. If the radiation dose of electron beam is less than 50 kGy, the bacterial cellulose would not be absorbed in vivo. On the other hand, if the radiation dose is more than 300 kGy, it would be waste and not economical because of the excessive energy consumption.

The bacterial cellulose herein is preferably the cellulose originated from a microorganism selected from the group consisting of *Acetobacter* sp., *Gluconacetobacter* sp., *Agrobacterium* sp., *Rhizobium* sp., *Pseudomonas* sp., and *Sarcina* sp., and more preferably the cellulose originated from *Acetobacter xylinum*, but not always limited thereto.

In general, when the bacterial cellulose is cultured in such a medium that includes carbon and nitrogen, a white thin film is formed on the surface of the culture medium. The formed bacterial cellulose has a high mechanical strength and is ultimately minute and has the three-dimensional network structure composed of pure cellulose. The general plant fiber is composed of cellulose, hemicellulose, and lignin, etc, but the bacterial cellulose is only composed of pure cellulose itself, so that it does not require any purification process. The film of the network structure is a randomly formed fibrillated cellulose in the shape of a ribbon which is composed of countless minute micro-fibrils whose width is smaller than 100 nm and radius is 2~4 nm. This bacterial cellulose micro fibril has the density of 1600 $kg/m^{-3}$ and has excellent biocompatibility since it has a uniquely higher crystallinity (84~89%) and strength (78 MPa) than the macro-scale natural fiber reported previously or similar Young's modulus to that of the glass fiber (70 GPa) in addition to enough pores.

The film generated from the bacterial cellulose can be cultured as the pure cellulose originated from *Acetobacter xylinum*, and at this time the culture method can be static cultivation or agitated cultivation, but static cultivation is more preferred. The bacterial cellulose cultured by agitated cultivation displays lower crystallinity and smaller size of crystals than the bacterial cellulose cultured by static cultivation, which is because cells are gathering in a circle due to the centrifugal force during the stirring in agitated cultivation and accordingly a cellulose negative mutant (cel−) can be generated instead of the bacterial cellulose owing to the shearing force.

The periodontal tissue or bone regeneration material is preferably one of the absorbable barrier membranes.

In a preferred embodiment of the present invention, the bacterial cellulose was irradiated in different conditions such as in freeze-dried state, in distilled water, and in PBS, with electron beam at the different doses (0, 25, 50, 100, and 300 kGy) in order to investigate the changes in the microstructure. As a result, it was confirmed that the microstructure of the bacterial cellulose is composed of the layers of cellulose fiber bundles with high density and the low density cellulose fibers are connected in between the high density layers above (see FIG. 1). As the radiation dose increased, the distance between the layers and the space between cellulose fibers were expanded. The difference in the structure according to the irradiation condition was investigated. As a result, the expansion of the distance between the layers and the space between cellulose fibers were increased as the following orders: dried<wet in distilled water<wet in PBS (see FIGS. 2~5). Therefore, it was suggested that the bacterial cellulose microstructure could be controlled by the irradiation condition and the radiation dose and such a structural change could affect the mechanical strength and physical properties of the bacterial cellulose.

The present inventors also confirmed that there was a change in the mechanical strength of the bacterial cellulose by irradiation. As the radiation dose increased, the tensile strength of the bacterial cellulose decreased (see FIGS. 6~8). From the investigation of the tensile strength according to the irradiation condition, it was confirmed that the bigger change was observed in the following order; the dried bacterial cellulose<the bacterial cellulose in distilled water<the bacterial cellulose in PBS (see FIG. 9). Therefore, it was confirmed that the changes in the physical properties of the bacterial cellulose were bigger when the bacterial cellulose was irradiated as wet in distilled water or in PBS, the radiation dose-dependently, consistently with the result of microstructure analysis (SEM) of the bacterial cellulose. The above result was believed to be attributed to the phenomenon that the hydrolysis of cellulose was induced by being wet in PBS or distilled water when irradiated. It was reported previously that the molecular weight of polysaccharide is reduced by irradiation. From the previous study, it was suggested that as the radiation dose increases, the molecular weight of cellulose decreases, resulting in the poor physical properties of the cellulose.

The present inventors also investigated whether or not the weight of each sample was decreased in the temperature range of 40~800° C., with increasing the temperature at the speed of 10° C./min in nitrogen environment, in order to investigate the thermo-stability and the pyrolysis behavior of the bacterial cellulose according to the radiation dose. Thermogravimetric analysis was performed with the dried bacterial cellulose irradiated with radiation. As a result, the early pyrolysis temperature was 250~270° C., and as the radiation dose was increased, the thermo-stability was decreased (see FIG. 10). When the bacterial cellulose was irradiated as wet in distilled water or PBS, the thermostability was decreased as the radiation dose was increased (see FIGS. 11 and 12). The pyrolysis temperature was lower when the bacterial cellulose was irradiated as wet in distilled water or PBS than when the bacterial cellulose was irradiated as dried (see FIG. 13). Therefore, the thermo-degradation of the bacterial cellulose could be controlled by regulating the irradiation condition and the radiation dose.

To investigate the changes in the chemical properties of the surface of the bacterial cellulose according to irradiation, ATR-FTIR spectrophotometry was performed. As a result, —OH stretching peak was observed at 3400 cm-1 and C—H stretching peak was observed at 2900 cm-1, which were not changed much after the irradiation with electron beam (see FIGS. 14~16).

To investigate the in vitro degradation of the bacterial cellulose according to the irradiation, the present inventors dipped the bacterial cellulose treated under the conditions as described above in 1×PBS (pH 7.4) and human serum like 5× simulated body fluid. Then the weight of the bacterial cellulose was compared with the original weight, with which the degradation rate was calculated by the mathematical formula below. As a result, the degradation rate of the bacterial cellulose irradiated as wet in PBS was slowly increased as the radiation dose increased, compared with the degradation rate of the sample irradiated as dried. In the meantime, the degradation rate of the bacterial cellulose irradiated as wet in SBF was rapidly increased as the radiation dose increased, compared with the degradation rate of the sample irradiated as dried (see FIGS. 17 and 18). This seemed because the molecular chains of the cellulose were cut off by the radiation ionizing energy generated by the ions included in the SBF solution.

To investigate the in vivo degradation of the bacterial cellulose over the time according to the irradiation, the present inventors opened the midback of SD rat and inserted the bacterial cellulose sample in the diameter of 8 mm in between the muscle tissue and the skin tissue medially. The animal was sacrificed, followed by the investigation of the in vivo degradation and histological examination. As a result, there was no difference among the rats one month after the irradiation, but the group transplanted with the bacterial cellulose and irradiated with 200 kGy displayed at least 50% absorptiveness 3 months after the irradiation. The group transplanted with the bacterial cellulose and irradiated with 100 kGy displayed about 30% absorptiveness. However, the group transplanted with the bacterial cellulose and irradiated with 0 and 50 kGy displayed no absorptiveness and the cellulose was gotten thicker (see FIG. 20). Hoping that the bacterial cellulose will maintain its morphology at least three months and will be completely absorbed about 6 months after the transplantation, the bacterial cellulose treated with 100 or 200 kGy is the most applicable candidate for the clinical use.

The present inventors developed a test model that copied the guided bone regeneration by inserting the artificial bone in a calvarial defected rat and covering the area with the conventional collagen barrier membrane and the bacterial cellulose barrier membrane of the invention. The inventors also evaluated the performance of the bacterial cellulose barrier membrane by the comparison with the conventional collagen barrier membrane. 4~8 weeks after the transplantation, the test rats were sacrificed. Autoradiography of the cranium was performed and the tissue sample was prepared, followed by observation. As a result, the performance as a barrier membrane of the bacterial cellulose of the invention was almost the same as the conventional collagen barrier membrane (see FIG. 21).

The present inventors performed histological examination for measuring the bone regeneration with the experimental group bacterial cellulose irradiated with 100~200 kGy which had been confirmed as the radiation dose that could allow the cellulose to be absorbed in the rat cranium and the comparative test animal, the calvarial defected rabbit. As a result, 8 weeks after the transplantation, bone was hardly regenerated in the control. The bacterial cellulose irradiated with 100 kGy maintained its shape as it was at the transplantation and the bacterial cellulose irradiated with 200 kGy was partially absorbed after the transplantation (see FIG. 24). The bacterial cellulose absorbed slowly could block the invasion of soft tissues for sure, suggesting it could be an ideal bone regeneration material. However, in the control group, the soft tissue invasion was strongly observed, suggesting that bone regeneration was not successfully induced (see FIG. 25).

Therefore, the bacterial cellulose of the present invention is advantageous since its biodegradability could be controlled by irradiation. The said bacterial cellulose was confirmed to block the invasion of soft tissue in the calvarial defected rat and rabbit models and to display excellent absorptiveness enough to contribute bone formation. So, the bacterial cellulose of the present invention can be used as an absorbable periodontal tissue and bone regeneration material necessary in the field of medical engineering without using chemicals which are harmful to human and environment.

The present invention also provides a barrier membrane for the inducement of absorbable periodontal tissue or bone regeneration comprising the irradiated bacterial cellulose as an active ingredient.

The radiation herein is preferably selected from the group consisting of gamma-ray, electron beam, x-ray, and ultraviolet (UV) rays, and more preferably electron beam, but not always limited thereto.

The radiation dose is preferably 100~300 kGy, and more preferably 150~250 kGy, but not always limited thereto. If the radiation dose of electron beam is less than 50 kGy, the bacterial cellulose would not be absorbed in vivo. On the other hand, if the radiation dose is more than 300 kGy, it would be waste and not economical because of the excessive energy consumption.

The bacterial cellulose herein is preferably the cellulose originated from a microorganism selected from the group consisting of *Acetobacter* sp., *Gluconacetobacter* sp., *Agrobacterium* sp., *Rhizobium* sp., *Pseudomonas* sp., and *Sarcina* sp., and more preferably the cellulose originated from *Acetobacter xylinum*, but not always limited thereto.

The present invention also provides a supporter for the regeneration of absorbable periodontal tissue or bone comprising the irradiated bacterial cellulose as an active ingredient.

The radiation herein is preferably selected from the group consisting of gamma-ray, electron beam, x-ray, and ultraviolet (UV) rays, and more preferably electron beam, but not always limited thereto.

The radiation dose is preferably 100~300 kGy, and more preferably 150~250 kGy, but not always limited thereto. If the radiation dose of electron beam is less than 50 kGy, the bacterial cellulose would not be absorbed in vivo. On the other hand, if the radiation dose is more than 300 kGy, it would be waste and not economical because of the excessive energy consumption.

The bacterial cellulose herein is preferably the cellulose originated from a microorganism selected from the group consisting of *Acetobacter* sp., *Gluconacetobacter* sp., *Agrobacterium* sp., *Rhizobium* sp., *Pseudomonas* sp., and *Sarcina* sp., and more preferably the cellulose originated from *Acetobacter xylinum*, but not always limited thereto.

The present invention also provides a method for the preparation of an absorbable periodontal tissue or bone regeneration material comprising the following steps:
1) pre-treating the bacterial cellulose; and
2) irradiating the pre-treated bacterial cellulose of step 1) with radiation.

The pre-treatment in step 1) of the method above is preferably drying, dipping in distilled water, or dipping in PBS, but not always limited thereto. The mechanical strength of the bacterial cellulose became weaker by irradiation when the bacterial cellulose was wet in distilled water or PBS, compared with when the bacterial cellulose was dried, which was because the distance between fiber layers and the space between fibers were expanded in the liquid.

The radiation herein is preferably selected from the group consisting of gamma-ray, electron beam, x-ray, and ultraviolet (UV) rays, and more preferably electron beam, but not always limited thereto.

The radiation dose is preferably 100~300 kGy, and more preferably 150~250 kGy, but not always limited thereto. If the radiation dose of electron beam is less than 50 kGy, the bacterial cellulose would not be absorbed in vivo. On the other hand, if the radiation dose is more than 300 kGy, it would be waste and not economical because of the excessive energy consumption.

In addition, the present invention provides a method for inhibiting the biodegradability of the bacterial cellulose and a method for increasing the flexibility and absorptiveness of the same comprising the following steps:
1) pre-treating the bacterial cellulose; and
2) irradiating the pre-treated bacterial cellulose of step 1) with radiation.

The pre-treatment in step 1) of the method above is preferably drying, dipping in distilled water, or dipping in PBS, but not always limited thereto. The mechanical strength of the bacterial cellulose became weaker by irradiation when the bacterial cellulose was wet in distilled water or PBS, compared with when the bacterial cellulose was dried, which was because the distance between fiber layers and the space between fibers were expanded in the liquid.

The radiation herein is preferably selected from the group consisting of gamma-ray, electron beam, x-ray, and ultraviolet (UV) rays, and more preferably electron beam, but not always limited thereto.

The radiation dose is preferably 100~300 kGy, and more preferably 150~250 kGy, but not always limited thereto. If the radiation dose of electron beam is less than 50 kGy, the bacterial cellulose would not be absorbed in vivo. On the other hand, if the radiation dose is more than 300 kGy, it would be waste and not economical because of the excessive energy consumption.

The bacterial cellulose of the present invention is advantageous since its biodegradability could be controlled by irradiation. The said bacterial cellulose was confirmed to block the invasion of soft tissue in the calvarial defected rat and rabbit models and to display excellent absorptiveness enough to contribute bone formation. So, the bacterial cellulose of the present invention can be used as an absorbable periodontal tissue and bone regeneration material necessary in the field of medical engineering without using chemicals which are harmful to human and environment.

Practical and presently preferred embodiments of the present invention are illustrative as shown in the following Examples.

However, it will be appreciated that those skilled in the art, on consideration of this disclosure, may make modifications and improvements within the spirit and scope of the present invention.

Example 1: Preparation of Bacterial Cellulose (BC)

The bacterial cellulose used in this invention was provided from JADAM Co. and all the reagents and solvents were used as they were without a purification process.

Particularly, the bacterial cellulose was obtained from the strain *Gluconacetobacter hansenii* TL-2C(KCG326). For the maintenance and pre-culture of the strain, glucose, yeast extract, $CaCO_3$, agar, and purified water were used. The basal medium for the pre-culture and main-culture was prepared by mixing glucose 10% (w/w), yeast extract 1% (w/w), $CaCO_3$ 2% (w/w), agar 1.5% (w/w), and proper amount of distilled water with regulating pH to be 6.8. For the pre-culture, the strain platinum loop preserved in agar plate was inoculated in the SPL Incu tissue culture vessel for plant tissue culture comprising 200 ml of the medium, followed by stationary culture at 27° C. for 48 hours. For the main culture, the pre-culture solution was inoculated [1% (w/w)] in a tray containing 1,300 ml of the medium, followed by stationary culture at 30° C. for 5 days. When a thin film was formed on the surface of the medium, the formed cellulose biofilm was treated with 0.25 M sodium hydroxide solution to eliminate the remaining bacteria and at the same time pure cellulose was separated. The film was washed with distilled water repeatedly and at last the bacterial cellulose was obtained.

Experimental Example 1: Changes in Microstructure of the Bacterial Cellulose by Irradiation To investigate the changes in microstructure of the bacterial cellulose of Example 1 by irradiation, the following experiment was performed.

Particularly, the bacterial cellulose of Example 1 (6 cm×6 cm) was irradiated with electron beam (UELV-10-10S, Russia) at different doses (0, 25, 50, 100, and 300 kGy) under the different conditions of being freeze-dried, being wet in distilled water, and wet in PBS, followed by investigation of the degradation rate of the bacterial cellulose. The samples irradiated with electron beam at different doses were freeze-dried, followed by investigation of the microstructure. To obtain high-resolution images of the bacterial cellulose, platinum coating was performed by using a sputter coater for 60 seconds for Scanning Electron Microscope (SEM). The high-resolution images of the bacterial cellulose were confirmed by SEM (JSM-6390, JEOL, Japan), and at that time the electron beam dose was 10 kV and the distance was set as 10~12 mm.

As a result, as shown in FIGS. 1~5, the microstructure of the bacterial cellulose was composed of the layers of high density cellulose fiber bundle and the layers therein were connected each other by those cellulose fibers displaying lower density than the cellulose fiber bundle forming the layer (FIG. 1). As the radiation dose increased, the distance between the layers and the space between the cellulose fibers were expanded (FIGS. 2~5). The difference in the structure according to the irradiation condition was investigated. As a result, the expansion of the distance between the layers and the space between the cellulose fibers were getting bigger in the following order: dried sample<sample in distilled water<sample in PBS (FIGS. 2~5).

Therefore, the microstructure of the bacterial cellulose can be controlled by the irradiation condition and the radiation dose. This structural change can affect the mechanical strength and physical properties of the bacterial cellulose.

TABLE 1

| | Irradiation condition |
|---|---|
| 1 | Irradiation onto the sample freeze-dried |
| 2 | Irradiation onto the sample sealed in distilled water |
| 3 | Irradiation onto the sample sealed in PBS |

Experimental Example 2: Changes in Mechanical Strength of the Bacterial Cellulose by Irradiation To investigate the changes in mechanical strength of the bacterial cellulose of Example 1 by irradiation, the following experiment was performed.

Particularly, tensile strength of the bacterial cellulose was measured by using universal testing machine (Instron Model-5569, Instron, USA) in order to measure the mechanical strength according to the structural changes caused by irradiation condition and radiation dose as shown in Table 1 of Experimental Example 1. The bacterial cellulose used in this experiment was prepared in the length of 30 mm and in the width of 5 mm. The measurement speed was 10 mm/min and the load was 5 kN.

As a result, as shown in FIGS. 6~9, as the radiation dose increased, the tensile strength of the bacterial cellulose decreased (FIGS. 6~8). As a result of the measurement of tensile strength according to the irradiation condition, as shown in FIG. 9, the changes in physical properties were getting bigger in the following order: dried sample<sample in distilled water<sample in PBS (FIG. 9).

Therefore, consistently with the result of SEM of the bacterial cellulose, the changes in physical properties of the bacterial cellulose were greater as the radiation dose increased when the sample was irradiated as wet in distilled water and in PBS. This seemed to be attributed to the fact that the cellulose was hydrolyzed in PBS and in distilled water by irradiation, which was also supported by the previous report saying that the molecular weight of polysaccharide decreases by irradiation. Therefore, it is believed that the physical properties of the bacterial cellulose become weaker as the radiation dose increases.

Experimental Example 3: Changes in Thermal Stability of the Bacterial Cellulose by Irradiation To investigate the changes in thermal stability and pyrolysis behavior of the bacterial cellulose of Example 1 by irradiation, the following thermal analysis was performed.

Particularly, the bacterial cellulose was analyzed with a thermogravimetric analyzer (TGA; TA Instrument Q600, USA) under the different conditions of irradiation and radiation dose as shown in Table 1 of Experimental Example 1. The weight of the sample bacterial cellulose was 15 mg and the analysis was performed with increasing the temperature from 40° C. to 800° C. at the raising speed of 10° C./min under nitrogen environment. The weight change of each sample was observed.

As shown in FIGS. 10~13, as a result of the thermogravimetric analysis of the sample irradiated in the dried condition, it was confirmed that the early pyrolysis temperature was 250~270° C., and the thermo-stability decreased as the radiation dose increased (FIG. 10). The thermo-stability of the samples irradiated as wet in distilled water and in PBS was also reduced as the radiation dose increased (Figures and 12). As shown in FIG. 13, the pyrolysis temperature was lower when the bacterial cellulose was irradiated as in distilled water or PBS than when the bacterial cellulose was irradiated as dried (FIG. 13).

Therefore, it was suggested that the thermo-degradation of the bacterial cellulose could be controlled by regulating the irradiation condition and the radiation dose.

Experimental Example 4: Changes in Chemical Surface Characteristics of the Bacterial Cellulose by Irradiation To investigate the changes in chemical surface characteristics of the bacterial cellulose of Example 1 by irradiation, the following experiment was performed.

Particularly, the bacterial cellulose irradiated under the conditions and radiation dose as shown in Table 1 of Experimental Example 1 was coated with hydroxyapatite (HA) in SBF (simulated body fluid), followed by analysis using ATR-FTIR spectrophotometer (Bruker TEMSOR 37, Bruker AXS. Inc., Germany).

As a result, as shown in FIGS. 14~16, —OH stretching peak of the bacterial cellulose was observed at 3400 cm$^{-1}$ cm-1 and C—H stretching peak was observed at 2900 cm$^{-1}$, which were hardly changed after the irradiation with electron beam (FIGS. 14~16). In the meantime, —OH stretching peak of the bacterial cellulose coated with HA in SBF was weakened. HA $PO_4^{3-}$ bending peak was observed at 1105, 1028, and 600 cm$^{-1}$, indicating that the bacterial cellulose was successfully coated with HA (non-patent references 4 and 5).

Experimental Example 5: Changes of In Vitro Degradation of the Bacterial Cellulose by Irradiation To investigate the changes of in vitro degradation of the bacterial cellulose of Example 1 by irradiation, the following experiment was performed.

Particularly, the bacterial celluloses, dried and dipped in liquid, were treated under the different conditions as shown in Experimental Example 1, which were then cut into 5 mm in diameter. Each section was dipped in 1× phosphate buffered saline (PBS, pH 7.4) and 5× simulated body fluid (SBF) for 4, 8, and 16 weeks. After collecting the samples 4, 8, and 16 weeks later, the samples were washed and freeze-dried. The weight of the dried sample was measured and compared with the original weight, with which the degradation rate was calculated by the mathematical formula below. The component and concentration of PBS and SBF are as shown in Table 2.

As a result, as shown in FIGS. 17 and 18, the degradation rate of the bacterial cellulose irradiated as being wet in PBS was slowly increased as the radiation dose increased, compared with the degradation rate of the sample irradiated as dried. In the meantime, the degradation rate of the bacterial cellulose irradiated as being wet in SBF was rapidly increased as the radiation dose increased, compared with the degradation rate of the sample irradiated as dried (FIGS. 17 and 18).

The result above was presumed because the molecular chains of the cellulose were cut off by the radiation ionizing energy generated by the ions included in the SBF solution.

TABLE 2

| 1 × PBS (Phosphate Buffered Saline) | 5 × SBF (Simulated Body Fluid) |
|---|---|
| 137.0 mM NaCl | 710.0 mM $Na^+$ |
| 2.70 mM KCl | 25.0 mM $K^+$ |
| 10 mM $Na_2HPO_4H_2O$ | 12.5 mM $Ca^{2+}$ |
| 2.00 mM $KH_2PO_4$ | 7.5 mM $MG^{2+}$ |
| 1.00 mM $CaCl_2$ | 21.0 mM $HCO_3$ |
| 0.50 mM $MgCl_2$ | 740 mM $Cl^-$ |
|  | 5.0 mM $HPO_4^{2-}$ |
|  | 2.5 mM $SO_4^{2-}$ |

Degradation rate=(late weight−early weight)/(early weight)×100   [Mathematical Formula 1]

Experimental Example 6: Changes of In Vivo Degradation of the Bacterial Cellulose by Irradiation To investigate the changes of in vivo degradation of the bacterial cellulose of Example 1 by irradiation, the following in vivo experiment was performed using animal models.

<6-1> Time Dependent Degradation Over

To investigate the in vivo degradation of the bacterial cellulose over the time according to the irradiation, the present inventors opened the midback of SD rat as shown in FIG. 19. The bacterial cellulose sample in the diameter of 8 mm was inserted in between the muscle tissue and the skin tissue. Then, the animal was sacrificed, followed by the investigation of in vivo degradation and histological examination.

Particularly, total 40 Sprague-Dawley rats (male, 250~300 g in weight) were used in this experiment. The bacterial cellulose samples were prepared in 4 groups irradiated with different radiation doses of 0, 50, 100, and 200 kGy. Animal selection, management, surgical protocol, and preparation were all performed according to the rules and regulations approved by Institutional Animal Care and Use Committee, Korea Atomic Energy Research Institute. 5 rats were allotted to each group of each period. All the surgical procedures were performed after general anesthesia by injecting the mixture of ketamine hydrochloride (KetalarYuhan, Seoul, Korea) and xylazine (Rumpun, Bayer Korea, Seoul, Korea) intra-muscularly. The target area for the transplantation of the bacterial cellulose sample was opened by surgical procedure and the skin was separated. The bacterial cellulose of Example 1 irradiated at different radiation doses of 0, 50, 100, and 200 kGy was transplanted in the subcutaneous tissue.

For the histological analysis, the present inventors prepared tissue samples by taking rat tissues after one month and three months after the transplantation of the bacterial cellulose in order to measure the absorptiveness for 3 months according to the radiation dose. The prepared samples were stained with H&E (hematoxylin and eosin) and Masson's trichrome in the center of each block, followed by histological examination.

As a result, the tissue samples taken from a month away from the transplantation demonstrated no difference over the radiation dose. In the meantime, as shown in FIG. 20, the group transplanted with the bacterial cellulose irradiated with 200 kGy displayed at least 50% absorptiveness 3 months after the transplantation. The group transplanted with the bacterial cellulose irradiated with 100 kGy displayed about 30% absorptiveness 3 months after the transplantation. The group transplanted with the bacterial cellulose irradiated with 0 and 50 kGy displayed no absorptiveness and the cellulose was gotten thicker (FIG. 20).

Hoping that the bacterial cellulose will maintain its morphology at least three months and will be completely absorbed about 6 months after the transplantation, the bacterial cellulose treated with 100 or 200 kGy is the most applicable candidate for the clinical use.

<6-2> Investigation of Performance of the Bacterial Cellulose Using the Calvarial Defected Rat Model The present inventors developed a test model that copied the guided bone regeneration by inserting the artificial bone in a calvarial defected rat and covering the area with the conventional collagen barrier membrane and the bacterial cellulose barrier membrane of the invention. The inventors also evaluated the performance of the bacterial cellulose barrier membrane by the comparison with the conventional collagen barrier membrane.

Particularly, total 40 Sprague-Dawley rats (male, 250~300 g in weight) were used in this experiment. The bacterial cellulose samples were prepared in 4 groups irradiated with different radiation doses of 0, 50, 100, and 200 kGy. Animal selection, management, surgical protocol, and preparation were all performed according to the rules and regulations approved by Institutional Animal Care and Use Committee, Korea Atomic Energy Research Institute. 5 rats were allotted to each group of each period. All the surgical procedures were performed after general anesthesia by injecting the mixture of ketamine hydrochloride (KetalarYuhan, Seoul, Korea) and xylazine (Rumpun, Bayer Korea, Seoul, Korea) intra-muscularly. To insert the bacterial cellulose sample in a test rat, the surgical site was opened as U shape. After moving up the full-thickness flap including skin and periosteum, a defect of 8 mm in diameter was made in the center of the cranium by using Trephine bur (3i Implant Innovation, Palm Beach Garden, Fla., USA). Then, bony disk was carefully removed. Collagen membrane (Control) and the bacterial cellulose of Example 1 irradiated with 0, 50, 100, or 200 kGy (Experimental group) were transplanted there.

For the histologic analysis, the center of each sample block was stained with H&E (hematoxylin and eosin) and Masson's trichrome. The tissue sample was observed under optical microscope. To measure the area of the new bone and the residual biomaterials, computer-assisted histometric measurement was performed by using image analysis computer program (Image-Pro Plus, Media Cybernetic, Silver Spring, Md., USA). The percentage of the new bone and the residual biomaterials to the defect area was calculated by the formula of FIG. 23.

For the statistical analysis, Kruskal-Wallis test was performed by using SPSS ver. 18.0 (SPSS, Chicago, Ill., USA) and posteriori test was performed by Mann-Whitney U test (p=0.05).

4~8 weeks after the transplantation, the test rats were sacrificed. Autoradiography of the cranium was performed and the tissue sample was prepared, followed by observation. As a result, as shown in FIG. 21, the performance as a barrier membrane of the bacterial cellulose of the invention was almost the same as the conventional collagen barrier membrane (FIG. 21).

<6-3> Investigation of Performance of the Bio-Cellulose Using the Calvarial Defected Rabbit Model Using the bacterial cellulose irradiated with 100 or 200 kGy that demonstrated absorptiveness in the rat cranium as the experimental group, the following experiment was performed with the calvarial defected rabbit.

Particularly, 6 New Zealand white rabbits (3.3~3.5 kg) were used in this experiment. The experiment was performed with the approval of Institutional Animal Care and Use Committee, Chonnam National University. The rabbit was anesthetized with the mixture of ketamine (75 mg/kg) and xylazine (10 mg/kg). Hair was removed from the cranium as shown in FIG. 22, and 4 round defects of 6 mm in diameter were made in there. The bacterial cellulose of Example 1 irradiated with 0 kGy (control), 100 kGy, and 200 kGy was transplanted into the bone defect. 4 weeks after the transplantation, the rabbit was sacrificed. 8 tissue samples were taken from each group to prepare tissue samples. The center of each sample block was stained with H&E and Masson's trichrome. The tissue sample was observed under optical microscope (BX50, Olympus, Tokyo, Japan). To measure the area of the new bone and the residual biomaterials, computer-assisted histometric measurement was performed by using image analysis computer program (Image-Pro Plus, Media Cybernetic, Silver Spring, Md., USA). The percentage of the new bone and the residual biomaterials to the defect area was calculated by the formula of FIG. 23. The control was not covered with a barrier membrane. In the defect area of the cranium was transplanted with hydroxyapatite synthetic bone, whose surface was covered with a barrier membrane, followed by analysis of the invasion of soft tissues and bone regeneration. 8 samples were taken from each group, followed by investigation for 8 weeks. Bone regeneration was investigated by histological analysis.

For the statistical analysis, Kruskal-Wallis test was performed by using SPSS ver. 18.0 (SPSS, Chicago, Ill., USA) and posteriori test was performed by Mann-Whitney U test ($p=0.05$).

As a result, as shown in FIGS. 24~26, 8 weeks after the transplantation, bone was hardly regenerated in the control. The bacterial cellulose irradiated with 100 kGy maintained its shape as it was at the transplantation and the bacterial cellulose irradiated with 200 kGy was partially absorbed after the transplantation (FIG. 24). The bacterial cellulose absorbed slowly could block the invasion of soft tissues for sure, suggesting it could be an ideal bone regeneration material. However, in the control group, the soft tissue invasion was strongly observed, suggesting that bone regeneration was not successfully induced (FIG. 25).

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A periodontal tissue or bone regeneration material comprising as an active ingredient bacterial cellulose that has been subject to electron beam irradiation, wherein the radiation dose is 100-300 kGy.

2. The periodontal tissue or bone regeneration material according to claim 1, wherein the bacterial cellulose is the cellulose originated from *Acetobacter xylinum*.

3. The periodontal tissue or bone regeneration material according to claim 1, wherein the material can have utility as an absorbable barrier membrane.

4. A barrier membrane for the inducement of absorbable periodontal tissue or bone regeneration comprising as an active ingredient bacterial cellulose that has been subject to electron beam irradiation, wherein the radiation dose is 100-300 kGy.

5. A support for the regeneration of absorbable periodontal tissue or bone comprising as an active ingredient bacterial cellulose that has been subject to electron beam irradiation, wherein the radiation dose is 100-300 kGy.

6. A method for the preparation of an absorbable periodontal tissue or bone regeneration material comprising the following steps:
 1) pre-treating the bacterial cellulose by drying, dipping in distilled water, or dipping in phosphate buffered saline (PBS); and
 2) irradiating the pre-treated bacterial cellulose of step 1) with electron beam radiation, wherein the radiation dose is 100-300 kGy.

7. A method for inhibiting the biodegradability of bacterial cellulose and increasing the flexibility and absorptiveness of the same, comprising the following steps:
 1) pre-treating the bacterial cellulose by drying, dipping in distilled water, or dipping in phosphate buffered saline (PBS); and
 2) irradiating the pre-treated bacterial cellulose of step 1) with electron beam radiation, wherein the radiation dose is 100~300 kGy.

* * * * *